(12) United States Patent
Yi et al.

(10) Patent No.: US 11,239,497 B2
(45) Date of Patent: *Feb. 1, 2022

(54) ELECTROLYTE AND ELECTROCHEMICAL DEVICE

(71) Applicant: Contemporary Amperex Technology Co., Limited, Ningde (CN)

(72) Inventors: Tiancheng Yi, Ningde (CN); Chunhua Hu, Ningde (CN); Lu Miao, Ningde (CN); Zijun Xu, Ningde (CN); Chengdu Liang, Ningde (CN)

(73) Assignee: Contemporary Amperex Technology Co., Limited, Ningde (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/370,973

(22) Filed: Mar. 30, 2019

(65) Prior Publication Data

US 2019/0326634 A1    Oct. 24, 2019

(30) Foreign Application Priority Data

Apr. 20, 2018  (CN) .......................... 201810362015.0

(51) Int. Cl.
| | | |
|---|---|---|
| *H01M 10/0567* | (2010.01) | |
| *C07D 239/04* | (2006.01) | |
| *C07D 241/04* | (2006.01) | |
| *C07D 251/04* | (2006.01) | |
| *H01M 10/0525* | (2010.01) | |
| *H01M 10/0568* | (2010.01) | |
| *H01M 10/0569* | (2010.01) | |

(52) U.S. Cl.
CPC ...... *H01M 10/0567* (2013.01); *C07D 239/04* (2013.01); *C07D 241/04* (2013.01); *C07D 251/04* (2013.01); *H01M 10/0525* (2013.01); *H01M 10/0568* (2013.01); *H01M 10/0569* (2013.01); *H01M 2300/0025* (2013.01)

(58) Field of Classification Search
None
See application file for complete search history.

(56) References Cited

U.S. PATENT DOCUMENTS

| | | | | |
|---|---|---|---|---|
| 10,868,334 B2 * | 12/2020 | Yi | ..................... | H01M 10/0567 |
| 2015/0064578 A1 | 3/2015 | Samsung | | |

FOREIGN PATENT DOCUMENTS

| | | | |
|---|---|---|---|
| CN | 102569886 A | | 7/2012 |
| CN | 103022556 A | | 4/2013 |
| CN | 103078140 A | | 5/2013 |
| CN | 103078140 B | | 4/2015 |
| CN | 103022556 B | | 6/2015 |
| CN | 105655639 A | | 6/2016 |
| CN | 107431197 A | | 12/2017 |
| EP | 3279998 A1 | | 2/2018 |
| JP | H11111332 A | | 4/1999 |
| JP | 2001357877 A | | 12/2001 |
| JP | 2008273893 A | | 11/2008 |
| JP | 2010-44883 | * | 2/2010 |
| JP | 2010044883 A | | 2/2010 |
| JP | 2012018801 A | | 1/2012 |
| WO | WO 2018/227689 | * | 12/2018 |

OTHER PUBLICATIONS

The first Office Action dated Mar. 9, 2020 for Japanese Application No. 2019-070308, 4 pages.
The first Office Action dated May 7, 2020 for Chinese Application No. 201810362015.0, 10 pages.
The extended European search report dated Sep. 5, 2019 for European Application No. 19166906.8, 9 pages.

* cited by examiner

*Primary Examiner* — Laura Weiner
(74) *Attorney, Agent, or Firm* — Law Offices of Liaoteng Wang

(57) ABSTRACT

This application provides an electrolyte and an electrochemical device, wherein the electrolyte comprises an additive A and an additive B, the additive A is present in an amount of 0.001% to 10% by mass in the electrolyte, and the additive B is present in an amount of 0.1% to 10% by mass in the electrolyte. This application can improve the cycle performance and storage performance of the electrochemical device, especially the cycle performance and storage performance of the electrochemical device under high temperature and high voltage conditions.

11 Claims, 1 Drawing Sheet

ELECTROLYTE AND ELECTROCHEMICAL DEVICE

CROSS-REFERENCE TO RELATED APPLICATION

Figure 1:
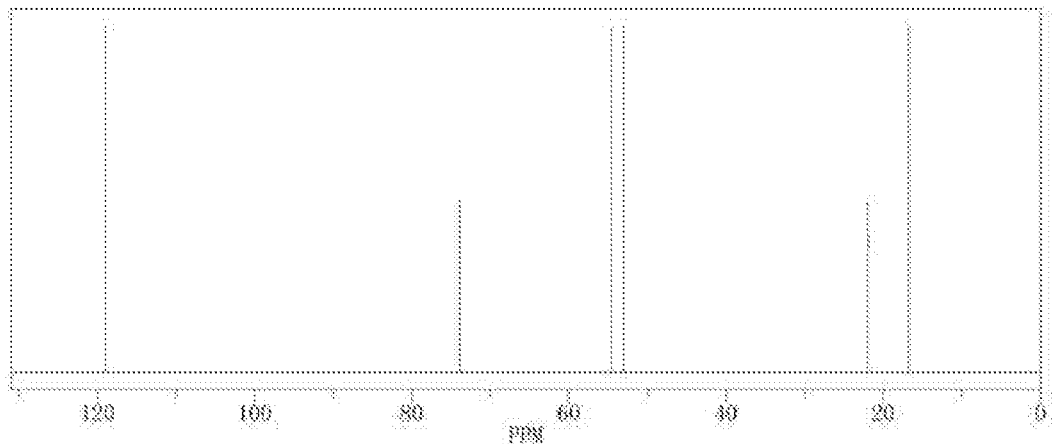

This application is based on and claims priority to Chinese Patent Application No. 201810362015.0 filed on Apr. 20, 2018, which is incorporated herein by reference in its entirety.

TECHNICAL FIELD

The present application relates to the field of energy storage materials, and in particular to an electrolyte and an electrochemical device.

BACKGROUND

Lithium-ion secondary batteries are widely used in electric vehicles and consumer electronics because of their high energy density, high output power, long cycle life and small environmental pollution. The current demand for lithium-ion secondary batteries is: high voltage, high power, long cycle life, long storage life and excellent safety performance.

Currently, the electrolyte system in which lithium hexafluorophosphate is used as a conductive lithium salt and a cyclic carbonate and/or a chain carbonate is used as an organic solvent is widely used for lithium-ion secondary batteries. However, the above electrolyte system still has many deficiencies. For example, under high voltage and high temperature conditions, the cycle performance and storage performance of the above electrolyte system need to be improved.

In view of this, the present application is specifically filed.

SUMMARY

In view of the problems in the prior art, the purpose of the present application is to provide an electrolyte and an electrochemical device, which can improve the cycle performance and storage performance of the electrochemical device, especially the cycle performance and storage performance of the electrochemical device under high temperature and high voltage conditions.

In order to achieve the above object, in a first aspect of the present application, the present application provides an electrolyte comprising an additive A and an additive B, wherein the additive A is present in an amount of 0.001% to 10% by mass in the electrolyte, and the additive B is present in an amount of 0.1% to 10% by mass in the electrolyte.

The additive A is selected from one or more of the compounds represented by Formula I-1, Formula I-2 and Formula I-3. In Formula I-1, Formula I-2, Formula I-3: $R_1$, $R_2$, $R_3$, $R_4$ are each independently selected from a hydrogen atom, a halogen atom, a substituted or unsubstituted $C_1$-$C_{12}$ alkyl group, a substituted or unsubstituted $C_1$-$C_{12}$ alkoxy group, a substituted or unsubstituted $C_1$-$C_{12}$ amino group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, and a substituted or unsubstituted $C_2$-$C_{12}$ heterocyclic group, wherein the substituent is selected from one or more of a halogen atom, a cyano group, a $C_1$-$C_6$ alkyl group, a $C_2$-$C_6$ alkenyl group, and a $C_1$-$C_6$ alkoxy group; wherein x, y, and z are each independently selected from an integer of 0 to 8; m, n, and k are each independently selected from an integer of 0 to 2.

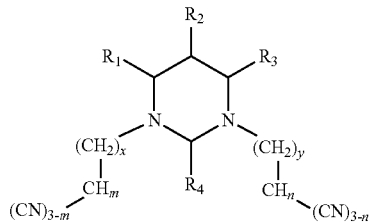

Formula I-1

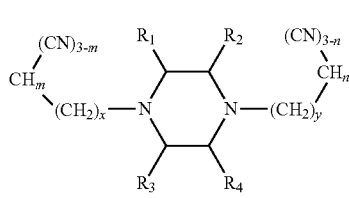

Formula I-2

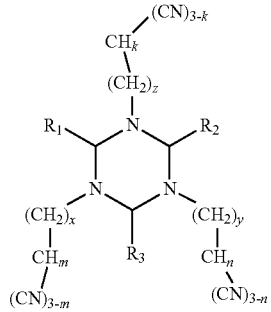

Formula I-3

The additive B is selected from the sulfonimide lithium salt of Formula II. In formula II, $R_F$ is one of $C_{p1}F_{2p1+1}$ and $F(CF_2CF_2O)_{q1}CF_2CF_2$, $R_f$ is one of $C_{p2}F_{2p2+1}$ and $F(CF_2CF_2O)_{q2}CF_2CF_2$; p1 and p2 are each independently selected from an integer of 0 to 8; and q1 and q2 are each independently selected from an integer of 1 to 6.

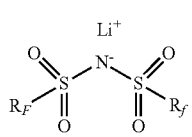

Formula II

In a second aspect of the present application, the present application provides an electrochemical device comprising a positive electrode plate, a negative electrode plate, a separator disposed between the positive electrode plate and the negative electrode plate, and the electrolyte according to the first aspect of the present application.

The technical solution of the present application has at least the following beneficial effects:

By adding a nitrogen-containing six-membered heterocyclic compound with more than one cyano group and sulfonimide lithium salt as an additive in the electrolyte of the present application, the surface of positive active materials can be effectively passivated, the surface activity of positive active materials can be suppressed, and the oxidation effect of the positive active materials on the electrolyte can be suppressed, and the storage gas production can be reduced while reducing side reactions. At the same time, the sulfonimide lithium salt has a high decomposition temperature and does not generate HF when decomposed. The sulfonimide lithium salt also may participate in the formation of SEI film on negative electrode, so that the formed negative electrode SEI film can hinder the direct contact of the negative electrode with the electrolyte, thereby further effectively reducing the occurrence of side reactions. Therefore, the above two additives synergistically improve the electrochemical performance of the electrochemical device under high temperature and high voltage conditions can be improved to a greater extent.

DRAWINGS

Figure 2:
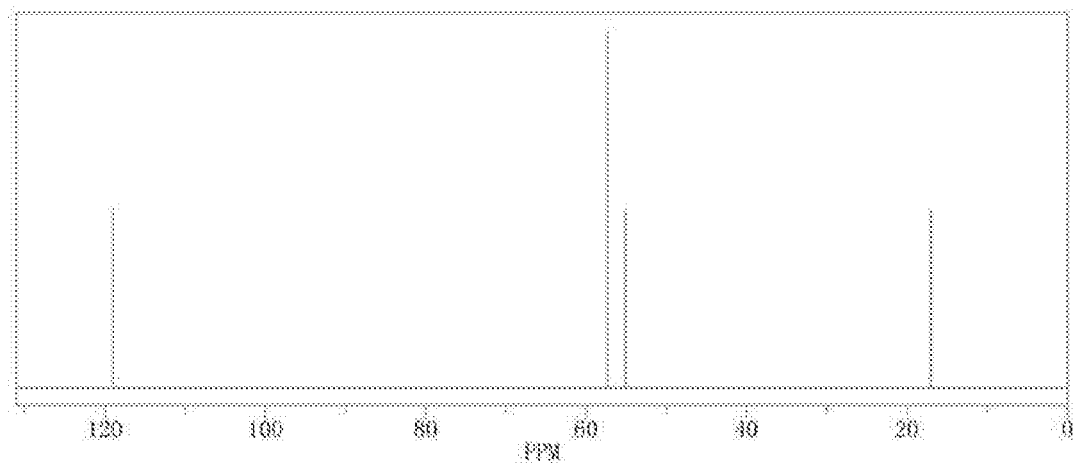
Figure 3:
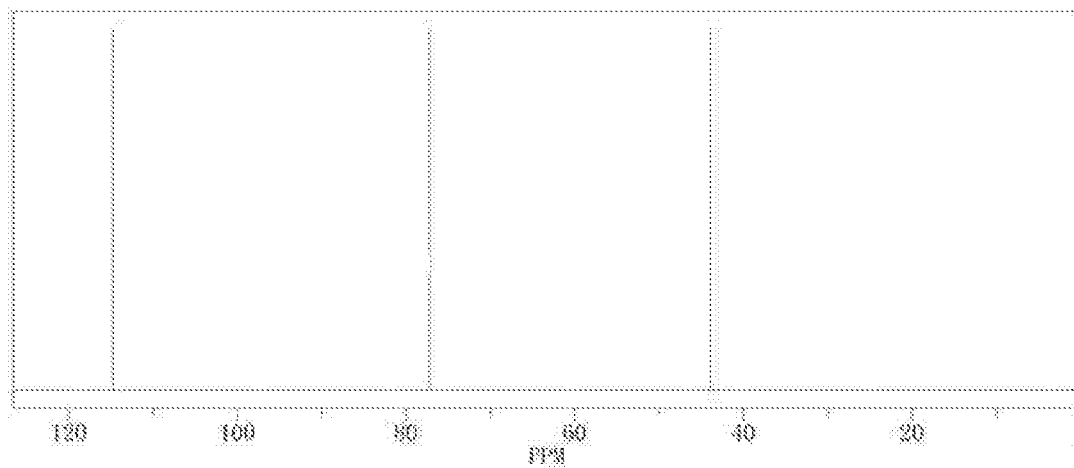

FIG. 1 is $C^{13}$ NMR spectrum of A2 compound.
FIG. 2 is $C^{13}$ NMR spectrum of A8 compound.
FIG. 3 is $C^{13}$ NMR spectrum of A13 compound.

DETAILED DESCRIPTION

The electrolyte and electrochemical device according to the present application will be described in detail below.

First, the electrolyte according to the first aspect of the present application will be explained.

The electrolyte according to the first aspect of the present application comprises an additive A and an additive B, wherein the additive A is present in an amount of 0.001% to 10% by mass in the electrolyte, and wherein additive B is present in an amount of 0.1% to 10% by mass in the electrolyte.

[Additive A]

In the electrolyte according to the first aspect of the present application, the additive A is selected from one or more of the compounds represented by Formula I-1, Formula I-2, and Formula I-3. In Formula I-1, Formula I-2, Formula I-3: $R_1$, $R_2$, $R_3$, $R_4$ are each independently selected from a hydrogen atom, a halogen atom, a substituted or unsubstituted $C^1$-$C_{12}$ alkyl group, a substituted or unsubstituted $C_1$-$C_{12}$ alkoxy group, a substituted or unsubstituted $C_1$-$C_{12}$ amino group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, and a substituted or unsubstituted $C_2$-$C_{12}$ heterocyclic group, wherein the substituent (in the case where a substitution occurs in "substituted or unsubstituted") is selected from one or more of a halogen atom, a cyano group, a $C_1$-$C_6$ alkyl group, a $C_2$-$C_6$ alkenyl group, and a $C_1$-$C_6$ alkoxy group; wherein x, y, and z are each independently selected from an integer of 0 to 8; m, n, and k are each independently selected from an integer of 0 to 2. In $R_1$, $R_2$, $R_3$, and $R_4$, the alkyl group, the alkenyl group, and the alkynyl group may be a chain structure or a cyclic structure, and the chain structure is further divided into a linear structure and a branched structure; and the halogen atom may be selected from one or more of a fluorine atom, a chlorine atom, and a bromine atom, preferably, a fluorine atom.

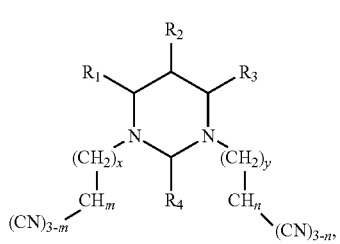

Formula I-1

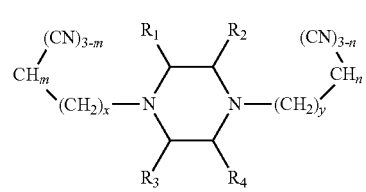

Formula I-2

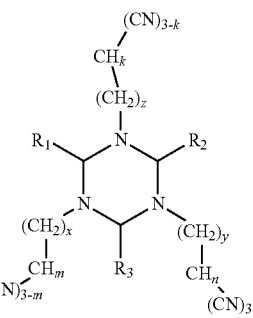

Formula I-3

In the electrolyte of the first aspect of the present application, the additive A is a nitrogen-containing six-membered heterocyclic compound with more than one cyano group, and the lone pair electrons contained in the nitrogen atom of the cyano group and the 3d empty orbit of the transition metal may have strong complexation. Therefore, when it is applied to the electrolyte, it can be adsorbed on the surface of positive active materials to form a layer of loose porous protective film, which can effectively passivate the surface of positive active materials, and isolating the surface of positive active materials from directly contacting with the electrolyte without affecting the normal transportation of ions, thus reduce the surface activity of positive active materials while inhibiting the oxidation effect thereof on the electrolyte, avoid a large number of side reactions on the surface of positive active materials, thereby reducing the side-products and reducing the gas production. In addition, the nitrogen-containing six-membered heterocyclic compound with more than one cyano group has a special nitrogen-containing six-membered heterocyclic structure, such that the distance between the cyano groups is closer to the distance between the transition metals on the surface positive active materials, and the complexation of the cyano group can be maximized, and a larger amount of cyano groups can play the role of complexation, to enhance the surface passivation effect of the positive active material; the special nitrogen-containing six-membered heterocyclic structure can also affect the film-formation potential of the cyano group and the film-forming effect on the surface of positive active material etc., which further improves the electrochemical performance of the entire system, such as reducing storage gas production, improving high-temperature and high-pressure cycle performance, and the like.

In the electrolyte according to the first aspect of the present application, the additive is present in an amount of 0.001% to 10% by mass in the electrolyte. If the content of the additive A is too low, its effect on improvement of the electrolyte is not significant, and if the content of the additive A is too high, the thickness of the complex layer as formed by its absorption on the surface of positive active materials is too large, then the positive electrode impedance is greatly increased, which deteriorates the performance of the electrochemical device. Preferably, the upper limit of the content of additive A may be optionally selected from 10%, 9%, 8%, 7%, 6%, 5%, 4.5%, 4%, 3.5%, 3%, 2%, 1%, and 0.8% by mass, and the lower limit of the content of additive A content may be optionally selected from 0.001%, 0.005%, 0.01%, 0.05%, 0.1%, 0.3%, 0.5%, 0.6%, 0.8%, 0.9%, 1.0%, and 1.2% by mass. Further preferably, the content of additive A in the electrolyte may be ranging from 0.01% to 6% by mass. Still more preferably, the content of additive A in the electrolyte may be ranging from 0.1% to 3.5% by mass.

In the electrolyte according to the first aspect of the present application, in the compounds of Formula I-1, Formula I-2, and Formula I-3:

The $C_1$-$C_{12}$ alkyl group may be a chain alkyl group or a cyclic alkyl group, and the chain alkyl group may be a linear alkyl group or a branched alkyl group, and the hydrogen located on the ring of the cyclic alkyl group may be further substituted by an alkyl group. The lower limit of the number of carbon atoms in the $C_1$-$C_{12}$ alkyl group is preferably 1, 2, 3, 4, and 5, and the upper limit is preferably 3, 4, 5, 6, 8, 10, and 12. Preferably, a $C_1$-$C_{10}$ alkyl group is used; more preferably, a $C_1$-$C_6$ chain alkyl group is used, a $C_3$-$C_8$ cyclic alkyl group is used; and still more preferably, a $C_1$-$C_4$ chain alkyl group or a $C_5$-$C_7$ cyclic alkyl group is used. Specific examples of the $C_1$-$C_{12}$ alkyl group include methyl, ethyl, n-propyl, isopropyl, n-butyl, isobutyl, sec-butyl, tert-butyl, n-pentyl, isopentyl, neopentyl, hexyl, 2-methyl-pentyl, 3-methyl-pentyl, 1,1,2-trimethyl-propyl, 3,3-dimethyl-butyl, heptyl, 2-heptyl, 3-heptyl, 2-methylhexyl, 3-methylhexyl, isoheptyl, octyl, nonyl and decyl.

In the case that the above-mentioned $C_1$-$C_{12}$ alkyl group contains an oxygen atom, it may be a $C_1$-$C_{12}$ alkoxy group. Preferably, a $C_1$-$C_{10}$ alkoxy group is used; further preferably, a $C_1$-$C_6$ alkoxy group is used; and still more preferably, a $C_1$-$C_4$ alkoxy group is used. Specific examples of the $C_1$-$C_{12}$ alkoxy group include methoxy group, ethoxy group, n-propoxy group, isopropoxy group, n-butoxy group, sec-butoxy group, tert-butoxy group, n-pentyloxy group, isopentyloxy group, cyclopentyloxy group and cyclohexyloxy group.

The $C_2$-$C_{12}$ alkenyl group may be a cyclic alkenyl group or a chain alkenyl group, and the chain alkenyl group may be a linear alkenyl group or a branched alkenyl group. Further, the number of double bonds in the $C_2$-$C_{12}$ alkenyl group is preferably one. The lower limit of the number of carbon atoms in the $C_2$-$C_{12}$ alkenyl group is preferably 2, 3, 4, and 5, and the upper limit is preferably 3, 4, 5, 6, 8, 10, and 12. Preferably, a $C_2$-$C_{10}$ alkenyl group is used; further preferably, a $C_2$-$C_6$ alkenyl group is used; and still more preferably, a $C_2$-$C_5$ alkenyl group is used. Specific examples of the $C_2$-$C_{12}$ alkenyl group include vinyl, allyl, isopropenyl, pentenyl, cyclohexenyl, cycloheptenyl, and cyclooctenyl.

The $C_2$-$C_{12}$ alkynyl group may be a cyclic alkynyl group or a chain alkynyl group, and the chain alkynyl group may be a linear alkynyl group or a branched alkynyl group. Further, the number of the triple bonds in the $C_2$-$C_{12}$ alkynyl groups is preferably one. The lower limit of the number of carbon atoms in the $C_2$-$C_{12}$ alkynyl group is preferably 2, 3, 4, and 5, and the upper limit is preferably 3, 4, 5, 6, 8, 10, and 12. Preferably, a $C_2$-$C_{10}$ alkynyl group is used; further preferably, a $C_2$-$C_6$ alkynyl group is used; and still more preferably, a $C_2$-$C_5$ alkynyl group is used. Specific examples of the $C_2$-$C_{12}$ alkynyl group include ethynyl, propargyl, isopropynyl, pentynyl, cyclohexynyl, cycloheptynyl, and cyclooctynyl.

The $C_1$-$C_{12}$ amino group may be selected from

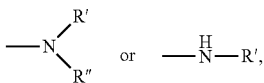

wherein R' and R" are selected from a $C_1$-$C_{12}$ alkyl group.

The $C_6$-$C_{26}$ aryl group may be a phenyl group, a phenylalkyl group, a biphenyl group, a fused polycylcic aromatic hydrocarbyl group (for example, a naphthyl group, an anthracenyl group, a phenanthryl group), wherein the biphenyl group and the fused polycylcic aromatic hydrocarbyl group may be further substituted by an alkyl or alkenyl group. Preferably, a $C_6$-$C_{16}$ aryl group is selected; further preferably, a $C_6$-$C_{14}$ aryl group is used; and still more preferably, a $C_6$-$C_9$ aryl group is used. Specific examples of the $C_6$-$C_{26}$ aryl group include phenyl, benzyl, biphenyl, p-methylphenyl, o-methylphenyl, m-methylphenyl, naphthyl, anthracenyl, and phenanthryl.

The hetero atom in the $C_2$-$C_{12}$ heterocyclic group may be selected from one or more of oxygen, nitrogen, sulfur, phosphorus, and boron, and the heterocyclic ring may be an aliphatic or aromatic heterocyclic ring. Preferably, a $C_2$-$C_{10}$ heterocyclic group is used; further preferably, a $C_2$-$C_7$ heterocyclic group is used; and still more preferably, a five-membered aromatic heterocyclic ring, a six-membered aromatic heterocyclic ring, or a benzoheterocyclic ring is used. Specific examples of the $C_2$-$C_{12}$ heterocyclic group include oxiranyl, oxetanyl, thiaranyl, aziridinyl, β-propiolactone, furanyl, thiophenyl, pyrrolyl, thiazolyl, imidazolyl, pyridinyl, pyrazinyl, pyrimidinyl, pyridazinyl, indolyl and quinolinyl.

(1) Specifically, the compound represented by Formula I-1 is a pyrimidine compound containing more than one cyano group.

In Formula I-1, it is preferred that $R_1$, $R_2$, $R_3$ and $R_4$ are each independently selected from a hydrogen atom, a fluorine atom, a chlorine atom, a bromine atom, a substituted or unsubstituted $C_1$-$C_6$ linear or branched alkyl group, a substituted or unsubstituted $C_5$-$C_9$ cyclic alkyl group, a substituted or unsubstituted $C_1$-$C_6$ alkoxy group, a substituted or unsubstituted $C_1$-$C_6$ amino group, a substituted or unsubstituted $C_2$-$C_6$ alkenyl group, a substituted or unsubstituted $C_2$-$C_6$ alkynyl group, a substituted or unsubstituted $C_6$-$C_{12}$ aryl group, and a substituted or unsubstituted $C_2$-$C_{12}$ heterocyclic group, wherein the substituent may be selected from one or more of the halogen atoms. It is further preferred that $R_1$, $R_2$, $R_3$ and $R_4$ are each independently selected from a hydrogen atom, a fluorine atom, a chlorine atom, a bromine atom, a substituted or unsubstituted $C_1$-$C_3$ linear or branched alkyl group, a substituted or unsubstituted $C_5$-$C_7$ cyclic alkyl group, a substituted or unsubstituted $C_1$-$C_3$ alkoxy group, a substituted or unsubstituted $C_1$-$C_3$ amino group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, and a substituted or unsubstituted $C_2$-$C_7$ heterocyclic group, wherein the substituent may be selected from one or more of halogen atoms.

In Formula I-1, x is preferably selected from an integer of 0 to 6, further preferably selected from an integer of 0 to 4, more preferably selected from 1 or 2.

In Formula I-1, y is preferably selected from an integer of 0 to 6, further preferably selected from an integer of 0 to 4, more preferably selected from 1 or 2.

In Formula I-1, it is preferred that $R_1$ and $R_3$ are the same group; and it is further preferred that $R_1$, $R_3$ and $R_4$ are all the same group.

In Formula I-1, it is preferred that $R_1$ and $R_3$ are each a hydrogen atom; it is further preferred that $R_1$, $R_3$ and $R_4$ are each a hydrogen atom; still it is still more preferred that $R_1$, $R_2$, $R_3$ and $R_4$ are each a hydrogen atom, or $R_1$, $R_3$ and $R_4$ are each a hydrogen atom, and $R_2$ is selected from a fluorine atom, a chlorine atom, a bromine atom, a substituted or unsubstituted $C_1$-$C_6$ linear or branched alkyl group, and a substituted or unsubstituted $C_1$-$C_6$ alkoxy group, wherein the substituent is selected from one or more of halogen atoms, and preferably, the substituent is selected from a fluorine atom.

Preferably, the compound represented by Formula I-1 may be specifically selected from one or more of the following compounds, but not limited thereto:

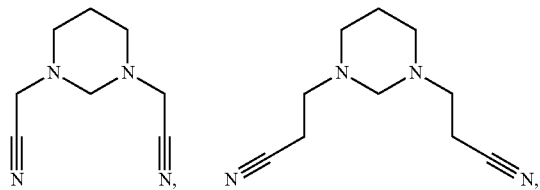

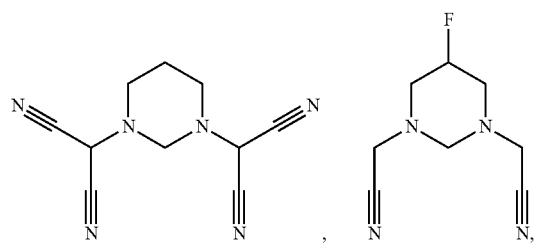

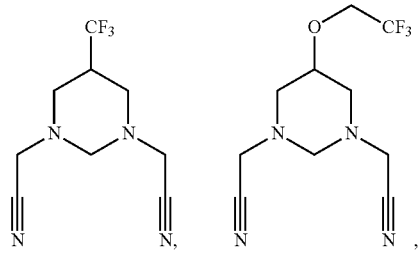

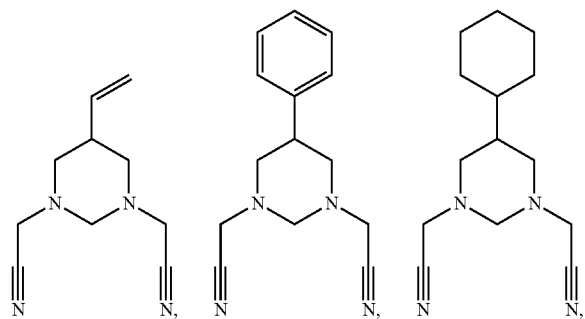

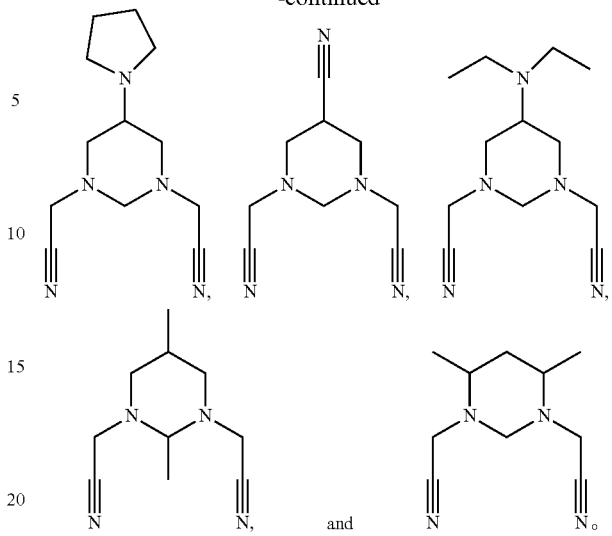

(2) Specifically, the compound represented by Formula I-2 is a piperazine compound containing more than one cyano group.

In Formula I-2, it is preferred that $R_1$, $R_2$, $R_3$ and $R_4$ are each independently selected from a hydrogen atom, a fluorine atom, a chlorine atom, a bromine atom, a substituted or unsubstituted $C_1$-$C_6$ linear or branched alkyl group, a substituted or unsubstituted $C_5$-$C_9$ cyclic alkyl group, a substituted or unsubstituted $C_1$-$C_6$ alkoxy group, a substituted or unsubstituted $C_1$-$C_6$ amino group, a substituted or unsubstituted $C_2$-$C_6$ alkenyl group, a substituted or unsubstituted $C_2$-$C_6$ alkynyl group, a substituted or unsubstituted $C_6$-$C_{12}$ aryl group, and a substituted or unsubstituted $C_2$-$C_{12}$ heterocyclic group, wherein the substituent is selected from one or more of halogen atoms. It is further preferred that $R_1$, $R_2$, $R_3$ and $R_4$ are each independently selected from a hydrogen atom, a fluorine atom, a chlorine atom, a bromine atom, a substituted or unsubstituted $C_1$-$C_3$ linear or branched alkyl group, a substituted or unsubstituted $C_5$-$C_7$ cyclic alkyl group, a substituted or unsubstituted $C_1$-$C_3$ alkoxy group, a substituted or unsubstituted $C_1$-$C_3$ amino group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, and a substituted or unsubstituted $C_2$-$C_7$ heterocyclic group, wherein the substituent is selected from one or more of halogen atoms.

In Formula I-2, x is preferably selected from an integer of 0 to 6, further preferably selected from an integer of 0 to 4, more preferably selected from 1 or 2.

In Formula I-2, y is preferably selected from an integer of 0 to 6, further preferably selected from an integer of 0 to 4, more preferably selected from 1 or 2.

In Formula I-2, it is preferred that at least two of $R_1$, $R_2$, $R_3$ and $R_4$ are the same group, and it is further preferred that at least three of $R_1$, $R_2$, $R_3$ and $R_4$ are the same group.

In Formula I-2, it is preferred that at least two of $R_1$, $R_2$, $R_3$ and $R_4$ are a hydrogen atom; and it is further preferred that at least three of $R_1$, $R_2$, $R_3$ and $R_4$ are a hydrogen atom; more preferably, $R_1$, $R_2$, $R_3$ and $R_4$ are each a hydrogen atom, or three of $R_1$, $R_2$, $R_3$ and $R_4$ are a hydrogen atom, and the remaining one is selected from a fluorine atom, a chlorine atom, a bromine atom, a substituted or unsubstituted $C_1$-$C_6$ linear or branched alkyl group, and a substituted or unsubstituted $C_1$-$C_6$ alkoxy group, wherein the substituent is selected from one or more of halogen atoms, and preferably, the substituent is selected from a fluorine atom.

Preferably, the compound of Formula I-2 may be specifically selected from one or more of the following compounds, but not limited thereto:

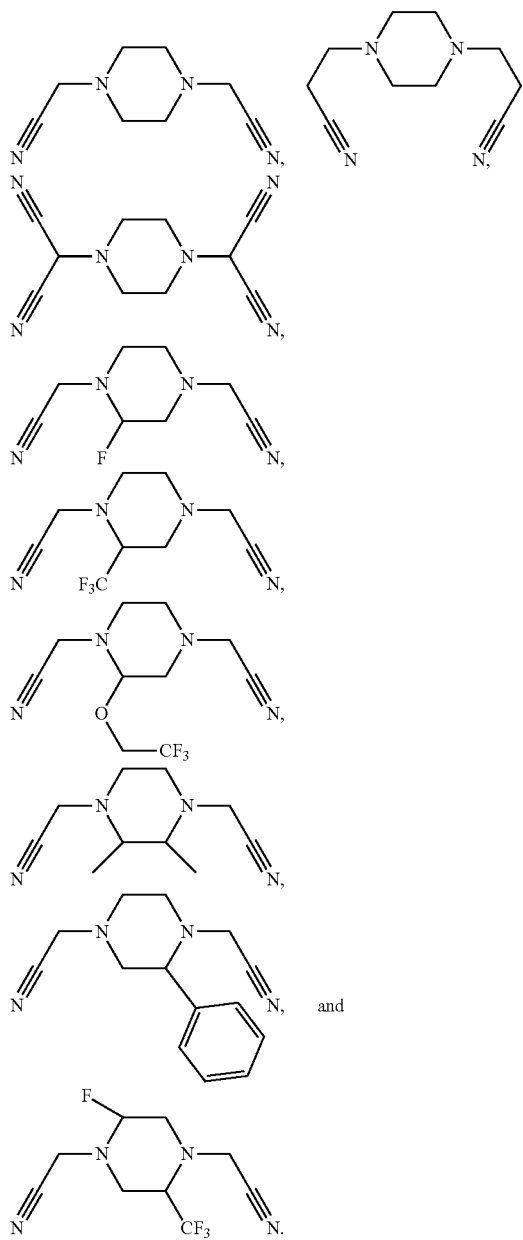

and (3) Specifically, the compound represented by Formula I-3 is a s-triazine compound containing more than one cyano group.

In Formula I-3, it is preferred that $R_1$, $R_2$ and $R_3$ are each independently selected from a hydrogen atom, a fluorine atom, a chlorine atom, a bromine atom, a substituted or unsubstituted $C_1$-$C_6$ linear or branched alkyl group, a substituted or unsubstituted $C_5$-$C_9$ cyclic alkyl group, a substituted or unsubstituted $C_1$-$C_6$ alkoxy group, a substituted or unsubstituted $C_1$-$C_6$ amino group, a substituted or unsubstituted $C_2$-$C_6$ alkenyl group, a substituted or unsubstituted $C_2$-$C_6$ alkynyl group, a substituted or unsubstituted $C_6$-$C_{12}$ aryl group, and a substituted or unsubstituted $C_2$-$C_{12}$ heterocyclic group, wherein the substituent is selected from one or more of halogen atoms. It is further preferred that $R_1$, $R_2$ and $R_3$ are each independently selected from a hydrogen atom, a fluorine atom, a chlorine atom, a bromine atom, a substituted or unsubstituted $C_1$-$C_3$ linear or branched alkyl group, a substituted or unsubstituted $C_5$-$C_7$ cyclic alkyl group, a substituted or unsubstituted $C_1$-$C_3$ alkoxy group, a substituted or unsubstituted $C_1$-$C_3$ amino group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, and a substituted or unsubstituted $C_2$-$C_7$ heterocyclic group, wherein the substituent is selected from one or more of halogen atoms.

In Formula I-3, x is preferably selected from an integer of 0 to 6, further preferably selected from an integer of 0 to 4, more preferably selected from 1 or 2.

In Formula I-3, y is preferably selected from an integer of 0 to 6, further preferably selected from an integer of 0 to 4, more preferably selected from 1 or 2.

In Formula I-3, it is preferred that at least two of $R_1$, $R_2$ and $R_3$ are the same group.

In Formula I-3, it is preferred that at least two of $R_1$, $R_2$, and $R_3$ are hydrogen atoms; and it is further preferred that $R_1$, $R_2$ and $R_3$ are each a hydrogen atom, or two of $R_1$, $R_2$ and $R_3$ are a hydrogen atom, and the remaining one is selected from a fluorine atom, a chlorine atom, a bromine atom, a substituted or unsubstituted $C_1$-$C_6$ linear or branched alkyl group, a substituted or unsubstituted $C_1$-$C_6$ alkoxy group, wherein the substituent is selected from one or more of halogen atoms, preferably, the substituent is selected from a fluorine atom.

Preferably, the compound represented by Formula I-3 may be specifically selected from one or more of the following compounds, but not limited thereto:

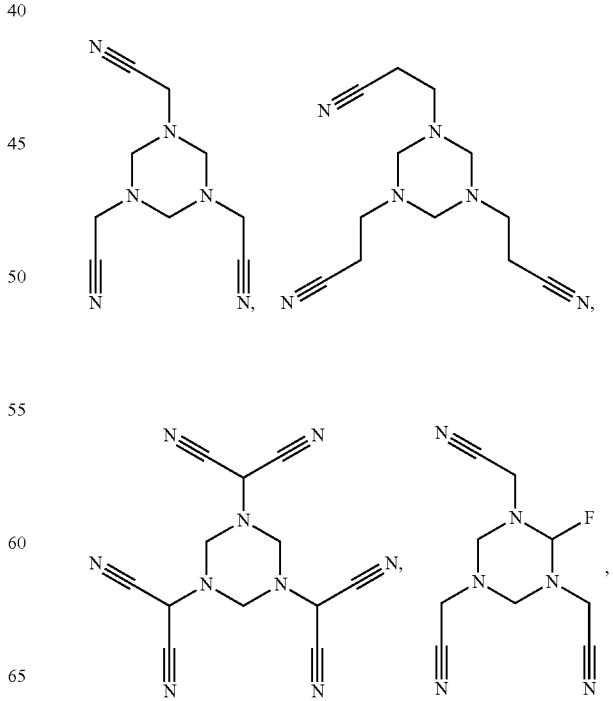

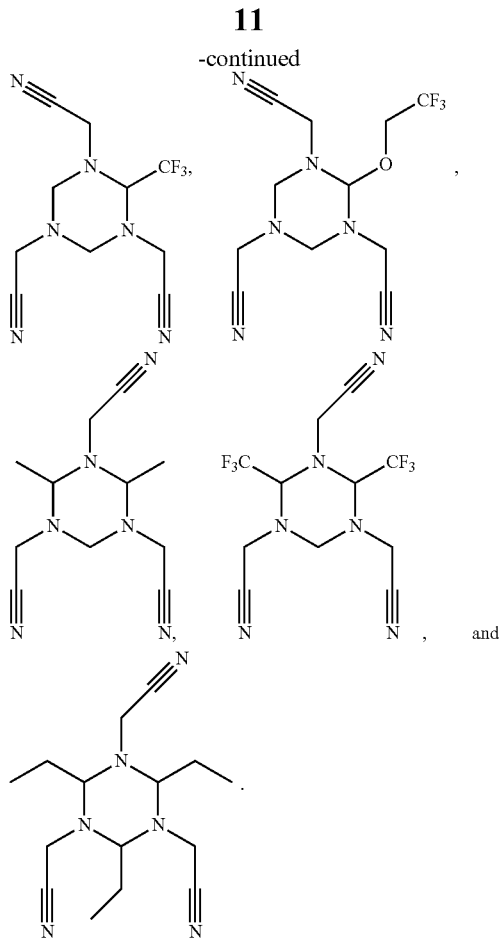

[Additive B]

In the electrolyte according to the first aspect of the present application, the additive B is selected from the sulfonimide lithium salt represented by Formula II.

Formula II

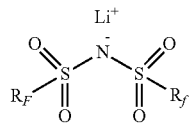

In Formula II, $R_F$ is one of $C_{p1}F_{2p1+1}$ and $F(CF_2CF_2O)_{q1}CF_2CF_2$, $R_f$ is one of $C_{p2}F_{2p2+1}$ and $F(CF_2CF_2O)_{q2}CF_2CF_2$; p1 and p2 are each independently selected from an integer of 0-8; q1 and q2 are each independently selected from an integer of 1 to 6.

Preferably, $R_F$ is $C_{p1}F_{2p1+1}$, $R_f$ is $C_{p2}F_{2p2+1}$, and p1 and p2 are each independently selected from an integer of 0 to 4.

Further preferably, the additive B is selected from one or more of the following compounds:

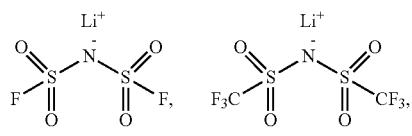

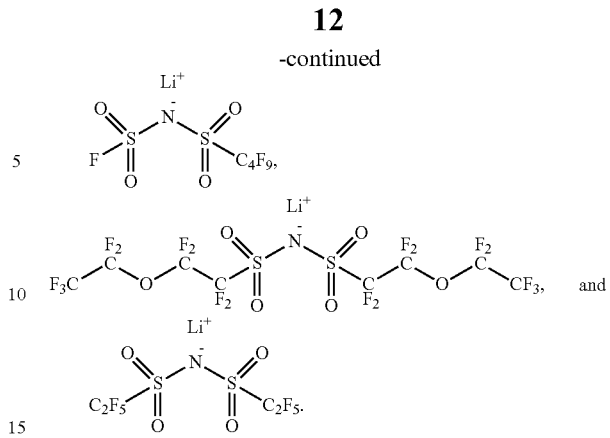

In the electrolyte according to the first aspect of the present application, on the one hand the additive B has a high decomposition temperature, and does not generate HF when decomposed, that is, having remarkably stronger than LiPF$_6$, so that it may remarkably improve the cycle performance and storage performance of the electrochemical device. On the other hand, it can also participate in the formation of SEI film on the negative electrode, so that the SEI film on the negative electrode can hinder the negative electrode from directly contacting with the electrolyte, thereby effectively reducing the occurrence of side reactions.

In the electrolyte according to the first aspect of the present application, the additive B is present in an amount of 0.1% to 10% by mass in the electrolyte. If the content of the additive B is too low, its effect on improvement of the electrolyte is not significant, and if the content of the additive B is too high, it will strongly corrode the positive current collector at a high voltage, and the cycle capacity retention ratio of the electrochemical device is lowered, which deteriorates the cycle performance of the electrochemical device. Preferably, the upper limit of the content of the additive B in the electrolyte may be optionally selected from 10%, 9%, 8%, 7%, 6%, 5%, 4.5%, 4%, 3.5%, 3%, 2%, and 1.5% by mass, and the lower limit may be optionally selected from 0.1%, 0.25%, 0.5%, 0.6%, 0.8%, 0.9%, 1.0%, and 1.2% by mass. Further preferably, the content of the additive B in the electrolyte is from 0.5% to 6% by mass. Still more preferably, the mass percentage of the additive B in the electrolyte is from 1% to 4% by mass.

[Additive C]

In the electrolyte according to the first aspect of the present application, the electrolyte may further comprise an additive C selected from one or more of a sulfate, a sulfite, and a sulfonate compound, wherein sulfonate compound is selected from one or more of a sultone compound and a disulfonate compound.

In the electrolyte according to the first aspect of the application, the sulfate compound is preferably a cyclic sulfate compound, and the cyclic sulfate compound may be selected from one or more of the compounds represented by Formula III-1. In Formula III-1, $R_{31}$ is selected from one or more of a substituted or unsubstituted $C_1$-$C_6$ alkylene group and a substituted or unsubstituted $C_2$-$C_6$ alkenylene group, wherein the substituent is selected from one or more of a halogen atom, a $C_1$-$C_3$ alkyl group, and a $C_2$-$C_4$ alkenyl group.

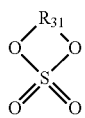

Formula III-1

Preferably, $R_{31}$ is selected from one or more of a substituted or unsubstituted $C_1$-$C_4$ alkylene group and a substituted or unsubstituted $C_2$-$C_4$ alkenylene group, wherein the substituent is selected from one or more of a halogen atom, a $C_1$-$C_3$ alkyl group, and a $C_2$-$C_4$ alkenyl group.

Further preferably, the sulfate compound may be specifically selected from one or more of the following compounds, but not limited thereto:

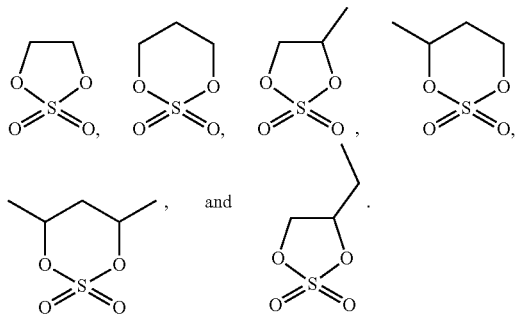

Still more preferably, the sulfate compound is selected from one or more of ethylene sulfate (i.e. 1,3,2-dioxathiolane 2,2-dioxide, abbreviated as DTD), trimethylene sulfite (abbreviated as TMS), and propylene sulfate (abbreviated as PLS), specifically the structures thereof are as follows:

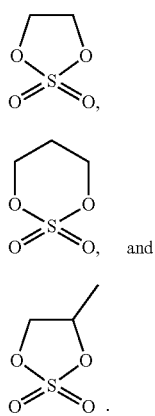

(DTD)

(TMS)

(PLS)

In the electrolyte according to the first aspect of the application, the sulfite compound is preferably a cyclic sulfite compound, and specifically may be selected from one or more of the compounds represented by Formula III-2. In Formula III-2, $R_{32}$ is selected from one or more of a substituted or unsubstituted $C_1$-$C_6$ alkylene group, and a substituted or unsubstituted $C_2$-$C_6$ alkenylene group, wherein the substituent is selected from one or more of a halogen atom, a $C_1$-$C_3$ alkyl group, and a $C_2$-$C_4$ alkenyl group.

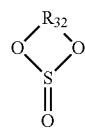

Formula III-2

Preferably, $R_{32}$ is selected from one or more of a substituted or unsubstituted $C_1$-$C_4$ alkylene group and a substituted or unsubstituted $C_2$-$C_4$ alkenylene group, wherein the substituent is selected from one or more of a halogen atom, a $C_1$-$C_3$ alkyl group, and a $C_2$-$C_4$ alkenyl group.

Further preferably, the sulfite compound may be selected from one or more of ethylene sulfite (abbreviated as ES), propylene sulfite (abbreviated as PS), and butylene sulfite (abbreviated as BS).

In the electrolyte according to the first aspect of the application, the sultone compound is selected from one or more of the compounds represented by Formula III-3, and in Formula III-3, $R_{21}$ is selected from one or more of a substituted or unsubstituted $C_1$-$C_6$ alkylene group and a substituted or unsubstituted $C_2$-$C_6$ alkenylene group, wherein the substituent is selected from one or more of a halogen atom, a $C_1$-$C_3$ alkyl group, and a $C_2$-$C_4$ alkenyl group.

Formula III-3

Preferably, $R_{21}$ is selected from one or more of a substituted or unsubstituted $C_1$-$C_4$ alkylene group and a substituted or unsubstituted $C_2$-$C_4$ alkenylene group, wherein the substituent is selected from one or more of a halogen atom, a $C_1$-$C_3$ alkyl group, and a $C_2$-$C_4$ alkenyl group.

Further preferably, the sultone compound may be specifically selected from one or more of the following compounds, but not limited thereto:

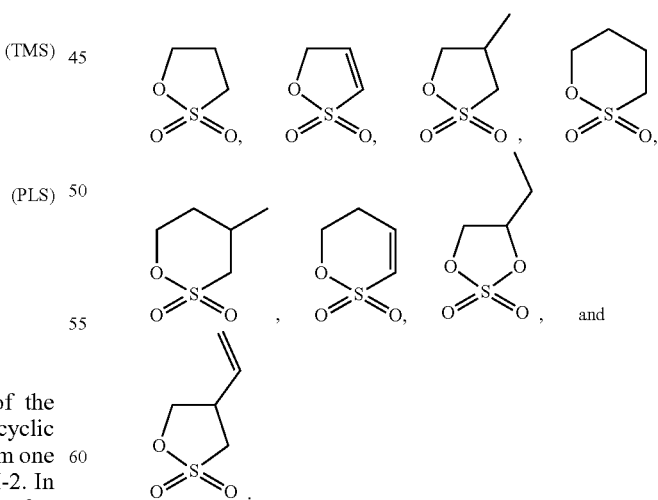

Still more preferably, the sultone compound may be selected from one or more of 1,3-propane sultone (abbreviated as PS) and 1,3-propene sultone (abbreviated as PES). The specific structures thereof are as follows:

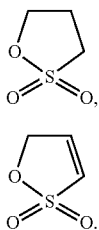

(PS)

(PES)

In the electrolyte according to the first aspect of the application, the disulfonate compound is a compound containing two sulfonic acid groups (—S(=O)$_2$O—), preferably selected from a methylene disulfonate compound, and the methylene disulfonate compound may be selected from one or more of the compounds represented by Formula III-4. In Formula III-4, $R_{22}$, $R_{23}$, $R_{24}$ and $R_{25}$ are each independently selected from one or more of a hydrogen atom, a halogen atom, a substituted or unsubstituted $C_1$-$C_{10}$ alkyl group, and a substituted or unsubstituted $C_2$-$C_{10}$ alkenyl group, wherein the substituent is selected from one or more of a halogen atom, a $C_1$-$C_3$ alkyl group, and a $C_2$-$C_4$ alkenyl group.

Formula III-4

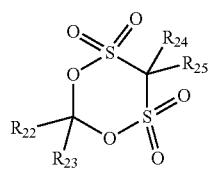

Preferably, $R_{22}$, $R_{23}$, $R_{24}$ and $R_{25}$ are each independently selected from one or more of a hydrogen atom, a halogen atom, a substituted or unsubstituted $C_1$-$C_4$ alkyl group, and a substituted or unsubstituted $C_2$-$C_6$ alkenyl group, wherein the substituent is selected from a one or more of a halogen atom, a $C_1$-$C_3$ alkyl group and a $C_2$-$C_4$ alkenyl group.

Further preferably, the disulfonate compound may be specifically selected from one or more of the following compounds, but not limited thereto:

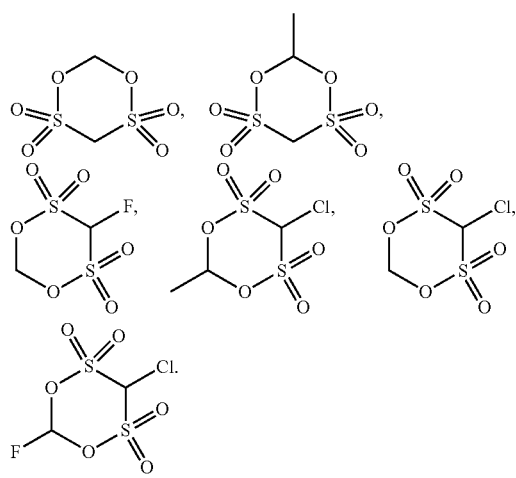

Still more preferably, the disulfonate compound may be selected from methylene methanedisulfonate (abbreviated as MMDS), and the specific structure is as follows:

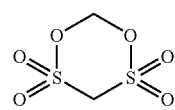

In the electrolyte according to the first aspect of the present application, the additive C has a higher reduction potential, and is preferentially reduced on the surface of the negative electrode in the electrolyte to form a dense sulfur-containing SEI film, preventing the solvation of lithium ions from destroying the structure of the negative active material. In addition, the oxidation potential of the additive C is also high, thus the additive C has good oxidation stability, and does not cause side reactions on the surface of the positive electrode.

In the electrolyte according to the first aspect of the present application, the content of the additive C in the electrolyte may be from 0.1% to 10% by mass. If the content of the additive C is too low, the effect on improvement of the electrolyte is not significant. If the content of the additive C is too high, the film formed on the surface of the positive electrode is too thick, and the cycle capacity retention ratio of the electrochemical device is lowered, which deteriorates the cycle performance of the electrochemical device. Preferably, the upper limit of the content of the additive C in the electrolyte may be optionally selected from 10%, 9%, 8%, 7%, 6%, 5%, 4.5%, 4%, 3.5%, 3%, 2%, and 1.5% by mass, and the lower limit may be optionally selected from 0.1%, 0.25%, 0.5%, 0.6%, 0.8%, 0.9%, 1.0%, and 1.2% by mass. Further preferably, the content of the additive C in the electrolyte is from 0.5% to 6% by mass. Still more preferably, the content of the additive C in the electrolyte is from 1% to 4% by mass.

In the electrolyte according to the first aspect of the present application, in Formula III-1, Formula III-2, Formula III-3, and Formula III-4:

The $C_1$-$C_6$ alkylene group may be a linear alkylene group or a branched alkylene group. The lower limit of the number of carbon atoms in the $C_1$-$C_6$ alkylene group is preferably 2 or 3; and preferably the upper limit is 4, 5, and 6. Preferably, a $C_1$-$C_4$ alkylene group is used. Specific examples of the $C_1$-$C_6$ alkylene group include methylene group, an ethylene group, a propylene group, an isopropylidene group, a butylene group, an isobutylene group, a sec-butylene group, a pentylene group, and a hexamethylene group.

The $C_2$-$C_6$ alkenylene group is a linear alkenylene group or a branched alkenylene group. The number of double bonds in the $C_2$-$C_6$ alkenylene group is preferably one. The number of carbon atoms in the $C_2$-$C_6$ alkenylene group preferably has a lower limit of 2, 3, and 4, and preferably the upper limit is 3, 4, 5, and 6. Preferably, a $C_2$-$C_5$ alkenylene group is used. Specific examples of the $C_2$-$C_6$ alkenylene group include a vinylidene group, an allylene group, an isopropenylene group, a butenylene group, and a pentenylene group.

In the electrolyte according to the first aspect of the present application, the electrolyte may be a liquid electrolyte, a solid electrolyte, or a gel electrolyte. An organic solvent, an electrolytic salt, a polymer, or the like may also be included in the electrolyte. In the present application, only the liquid electrolyte is further described in detail.

[Organic Solvents]

The organic solvent used in the electrolyte of the embodiment of the present application comprises a cyclic carbonate and a chain carbonate, which may further improve cycle performance and storage performance under high temperature and high voltage, and which is favorable for the additive film A and additive B to achieve a better film forming effect.

Specifically, the cyclic carbonate may be selected from the cyclic carbonate such as ethylene carbonate, propylene carbonate, 1,2-butylene carbonate, and 2,3-butylene glycol carbonate.

Specifically, the chain carbonate may be an asymmetric chain carbonate selected from one or more of ethyl methyl carbonate, methyl propyl carbonate, methyl isopropyl carbonate, methyl butyl carbonate, and ethyl propyl carbonate; or a symmetric chain carbonate, preferably selected from one or more of dimethyl carbonate, diethyl carbonate, dipropyl carbonate and dibutyl carbonate; and may also be a mixture of an asymmetric chain carbonate and a symmetric chain carbonate.

The organic solvent may further comprise a carboxylic acid ester. That is to say, the organic solvent according to the present application may comprise a mixture of a cyclic carbonate, a chain carbonate, and a carboxylic acid ester. Carboxylic acid esters have the characteristics of large dielectric constant and low viscosity, which can effectively prevent the association of lithium ions and anions in the electrolyte, and have more advantages in ion conduction than cyclic carbonates and chain carbonates.

Specifically, the carboxylic acid ester may be selected from one or more of methyl pivalate, ethyl pivalate, propyl pivalate, butyl pivalate, methyl butyrate, ethyl butyrate, propyl butyrate, butyl butyrate, methyl propionate, ethyl propionate, propyl propionate, butyl propionate, methyl acetate, ethyl acetate, propyl acetate and butyl acetate.

[Electrolytic Salt]

As the electrolytic salt used in the present application, the following lithium salt can be suitably exemplified.

[Li salt-Type I]: It may be "a complex salts of Lewis acid with LiF" suitably selected from one or more of $LiPF_6$, $LiBF_4$, $LiAsF_6$, $LiSbF_6$, $LiPF_4(CF_3)_2$, $LiPF_3(C_2F_5)_3$, $LiPF_3(CF_3)_3$, $LiPF_3(iso-C_3F_7)_3$, and $LiPF_5$ (iso-C3F7), preferably from $LiPF_6$, $LiBF_4$, $LiAsF_6$, and more preferably from $LiPF_6$ and $LiBF_4$.

[Li salt-Type II]: It may be "an imine or methylated lithium salt" suitably selected from one or more of $(CF_2)_2(SO_2)_2NLi$ (cyclic), $(CF_2)_3(SO_2)_2NLi$ (cyclic), and $LiC(SO_2CF_3)_3$.

[Li salt-Type III]: It may be "a lithium salt containing the structure of $S(=O)_2O$" suitably selected from one or more of $LiSO_3F$, $LiCF_3SO_3$, $CH_3SO_4Li$, $C_2H_5SO_4Li$, $C_3H_7SO_4Li$, lithium trifluoro((methylsulfonyl)oxy)borate (LiTFMSB), lithium pentafluoro((methylsulfonyl)oxy) phosphate (LiPFMSP), more preferably from $LiSO_3F$, $CH_3SO_4Li$, $C_2H_5SO_4Li$ or LiTFMSB.

[Li salt-Type IV]: It may be "lithium salt containing a P=O or Cl=O structure" suitably selected from one or more of $LiPO_2F_2$, $Li_2PO_3F$ and $LiClO_4$, preferably from $LiPO_2F_2$, $Li_2PO_3F$.

[Li salt-Type V]: It may be "lithium salt with an oxalate ligand as an anion ion" suitably selected from lithium bis[oxalate-O,O'] borate (LiBOB), lithium difluoro [oxalate-O, O'] borate, lithium difluorobis[oxalate-O,O'] phosphate (LiPFO) and lithium tetrafluoro [oxalate-O,O'] phosphate, more preferably from LiBOB and LiPFO.

The above lithium salts may be used alone or in combination. Preferably, the lithium salt is selected from one or more of $LiPF_6$, $LiPO_2F_2$, $Li_2PO_3F$, $LiBF_4$, $LiSO_3F$, lithium trifluoro((methyl sulfonyl)oxy)borate (LiTFMSB), lithium bis[oxalate-O,O'] borate (LiBOB), lithium difluorobis[oxalate-O,O'] phosphate (LiPFO) and lithium tetrafluoro [oxalate-O,O'] phosphate. More preferably, the lithium salt is selected from one or more of $LiPF_6$, $LiBF_4$, $LiSO_3F$, lithium trifluoro((methylsulfonyl)oxy)borate (LiTFMSB), $LiPO_2F_2$, lithium bis[oxalate-O,O'] borate (LiBOB) and lithium difluorobis[oxalate-O,O'] phosphate (LiPFO). Further preferably, the lithium salt is $LiPF_6$.

In the electrolyte according to the first aspect of the present application, the preparation method of the electrolyte is not limited, and it can be prepared according to the conventional method for preparing an electrolyte. For example, it can be obtained by mixing the above organic solvents, adding an electrolyte salt thereto, and adding each additive thereto.

In the electrolyte according to the first aspect of the present application, the additive A can be synthesized by the following method.

Synthesis of the Compound of Formula I-1:

The reaction equation is:

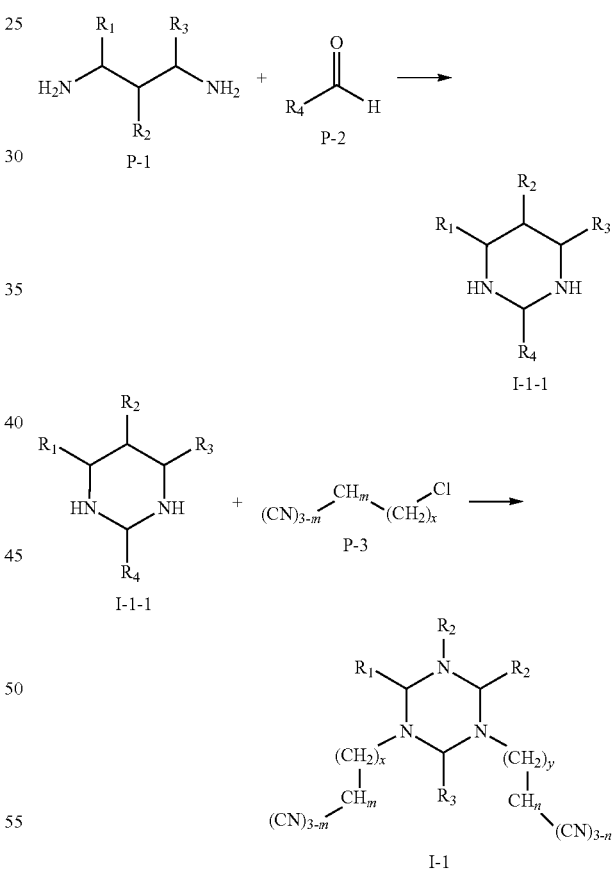

The specific preparation process is:

P-2 aqueous solution with a concentration of 30%~40% was added dropwise to the raw material P-1 in 20 min to 60 min and stirred rapidly. After the completion of the dropwise addition, the mixture was rapidly stirred for 15-30 h, and stirred at 70° C. to 90° C. for 3-5 h in an oil bath, to obtain colorless fuming viscous liquid intermediate I-1-1; then $K_2CO_3$, KI and anhydrous acetonitrile were added, and the mixture was rapidly stirred into a solid-liquid mixed phase, and raw material P-3 was quickly added at 40° C. to 60° C. After stirring for 10 h to 20 h, the resulting mixture was cooled to room temperature, and isolated and purified to obtain a compound of Formula I-1.

(2) Preparation of a Compound Represented by Formula I-2:

The reaction equation is:

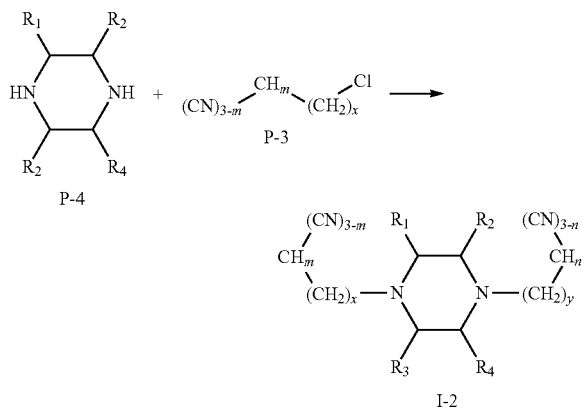

The specific preparation process is:

The anhydrous sodium carbonate, the raw material P-4 and the raw material P-3 were mixed in absolute ethanol, and the mixture was stirred for 2 to 5 hours, then washed with hot ethanol for several times to obtain a crude product, which was then recrystallized to obtain a compound represented by Formula I-2.

(3) Preparation of a Compound Represented by Formula I-3:

The reaction equation is:

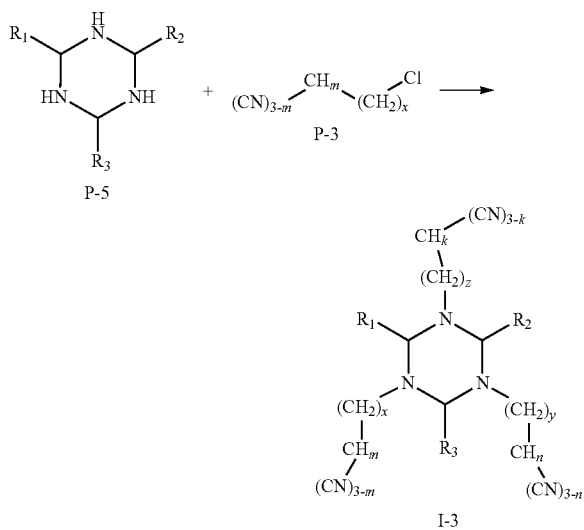

The specific preparation process is:

The anhydrous sodium carbonate, the raw material P-5 and the raw material P-3 were mixed in absolute ethanol, and the mixture was stirred for 2 to 5 hours, then washed with hot ethanol for several times to obtain a crude product, which was then recrystallized to obtain a compound represented by Formula I-3.

An electrochemical device according to the second aspect of the present application is explained below.

The electrochemical device according to the second aspect of the present application comprises a positive electrode plate, a negative electrode plate, a separator disposed between the positive electrode plate and the negative electrode plate, and an electrolyte according to the first aspect of the present application. It should be noted that the electrochemical device according to the second aspect of the present application may be a lithium-ion secondary battery, a lithium-ion primary battery or a lithium-ion capacitor.

When the electrochemical device is a lithium-ion secondary battery, the positive electrode comprises a positive active material capable of deintercalating and intercalating lithium ions, and the negative electrode comprises a negative active material capable of intercalating and deintercalating lithium ions. Specifically, the positive active material may be selected from one or more of lithium cobalt oxide, lithium nickel oxide, lithium manganese oxide, lithium nickel manganese oxide, lithium nickel cobalt manganese oxide, lithium nickel cobalt aluminum oxide, and a compound obtained by adding other transition metal or non-transition metal to the above oxides. Specifically, a layered lithium-containing oxide, a spinel-type lithium-containing oxide, an olivine-type lithium-containing phosphate compound, or the like can be used. However, the present application is not limited to these materials, and other conventionally known materials which can be used as a positive active material for a lithium-ion secondary battery can also be used. These positive active materials may be used alone or in combination of two or more. The negative active material may be soft carbon, hard carbon, artificial graphite, natural graphite, silicon, silicon oxide, silicon carbon composite, lithium titanium oxide, and the metal which can form an alloy with lithium, etc. Specifically, a carbon-based material, a silicon-based material, a tin-based material, or the like can be used. However, the present application is not limited to these materials, and other conventionally known materials which can be used as a negative active material for a lithium-ion secondary battery can also be used. These negative e active materials may be used alone or in combination of two or more.

When the electrochemical device is a lithium-ion primary battery, specifically, the negative active material is metallic lithium or a lithium alloy. The positive active material may be a solid halide such as copper fluoride ($CuF_2$), copper chloride ($CuCl_2$), silver chloride (AgCl), polyfluorocarbon (($CF)_4$); a solid sulfide such as copper sulfide (CuS), iron sulfide (FeS), iron disulfide ($FeS_2$); a solid oxide such as manganese dioxide ($MnO_2$), copper oxide (CuO), molybdenum trioxide ($MoO_3$), vanadium pentoxide ($V_2O_5$). The positive electrode active material may also be a solid oxyacid salt such as silver chromate ($Ag_2CrO_4$) or lead bismuthate ($Pb_2Bi_2O_5$). These positive active materials may be used alone or in combination of two or more.

When the electrochemical device is a lithium-ion capacitor, the negative active material of the lithium-ion capacitor is graphite or a polyacene material, and the positive active material is activated carbon.

In the electrochemical device according to the second aspect of the present application, the specific kind of the separator is not particularly limited, and may be any separator material used in the existing electrochemical device, such as polyethylene, polypropylene, polyvinylidene fluoride, and multilayer composite film thereof, but not limited to these.

In the electrochemical device according to the second aspect of the present application, the positive electrode plate further comprises a binder and a conductive agent. A positive electrode slurry containing a positive active material, a binder, and a conductive agent is coated on the positive electrode current collector, and a positive electrode plate is obtained after the positive electrode slurry is dried. Similarly, the negative electrode plate further comprises a binder and a conductive agent. A negative electrode slurry containing a negative active material, a binder, and a conductive agent is coated on the negative electrode current collector, and a negative electrode plate is obtained after the negative electrode slurry is dried.

Further, when the electrochemical device is a lithium-ion secondary battery, the charge cutoff voltage of the lithium-ion secondary battery is not less than 4.2 V, that is to say, the lithium-ion secondary battery can be used in a high voltage state of not less than 4.2 V. Preferably, the lithium-ion secondary battery can work in the range of 4.2 V to 4.9 V, and further preferably, the lithium-ion secondary battery works in the range of 4.3 V to 4.8 V. In the high voltage state, the higher the valence state of the transition metal on the surface of the positive active material is, the more electrons are lost, the more empty orbits are formed, and the more easily the orphan electrons of the nitrogen atom in the additive A are complexed, that is to say, the additive A can play the corresponding protection role to a greater extent.

In order to make the objects, technical solutions and beneficial technical effects of the present application more clear, the present application will be further described in detail below with reference to the embodiments. It is to be understood that the embodiments described in the specification are merely illustrative of the application, and are not intended to limit the scope of the application.

In the following specific embodiments of the present application, only the embodiment in which the electrochemical device is a lithium-ion secondary battery is shown, but the application is not limited thereto. In the examples and comparative examples, the reagents, materials, and instruments used are commercially available unless otherwise specified. The specific synthesis process of the additives A2, A8, and A13 is as follows, and other kinds of additives A can be synthesized according to a similar process.

Synthesis of Additive A2:

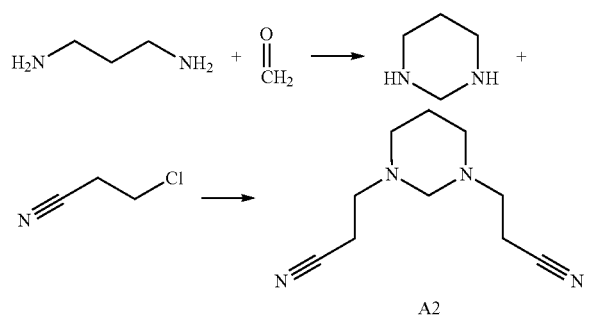

37% formaldehyde aqueous solution is added dropwise to 1,3-propanediamine in 0.5 h and stirred rapidly. After the completion of the dropwise addition, rapid stirring is continued for 20 h, followed by refluxing in an oil bath at 80° C. for 4 h to obtain a colorless fuming viscous liquid, i.e. the intermediate product hexahydropyrimidine; continue to add K$_2$CO$_3$, KI, anhydrous acetonitrile, quickly stir into a solid-liquid mixed phase, then add β-chloropropionitrile in 0.5 h at 60° C., continue stirring for 17 h, then cool to room temperature. After separation and purification, A1 is obtained. The nuclear magnetic resonance spectrum is shown in FIG. 1.

Synthesis of Additive A8:

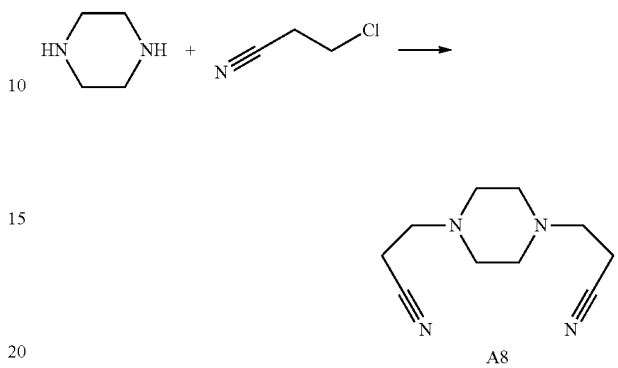

Anhydrous sodium carbonate, piperazine and β-chloropropionitrile are mixed in absolute ethanol, and the reaction was stirred for 4 hours; the resulting mixture is washed with hot ethanol for several times to obtain a crude product, which is recrystallized to obtain A8. The nuclear magnetic resonance spectrum is shown in FIG. 2.

Synthesis of Additive A13:

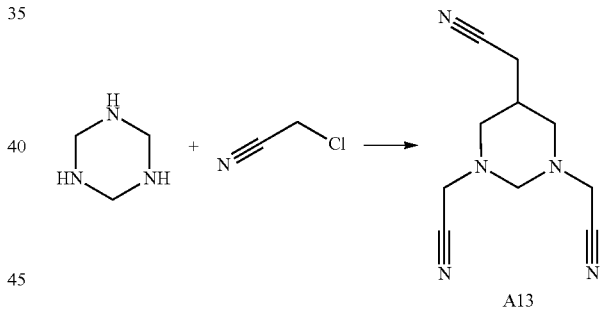

Anhydrous sodium carbonate, 1,3,5-triazine and chloroacetonitrile are mixed in absolute ethanol, and the reaction is stirred for 4 hours; the resulting mixture is washed with hot ethanol for several times to obtain a crude product, which is recrystallized to obtain A13. The nuclear magnetic resonance spectrum is shown in FIG. 3.

In the examples and comparative examples, lithium-ion secondary batteries were prepared in the following manner.

(1) Preparation of electrolyte: The mixture of ethylene carbonate (abbreviated as EC), ethyl methyl carbonate (abbreviated as EMC) and diethyl carbonate (abbreviated as DEC) was used as an organic solvent, wherein the mass ratio of EC, EMC and DEC was 1:1:1. The lithium salt was LiPF$_6$, and the total content of LiPF$_6$ was 12.5% based on the total mass of the electrolyte. Each additive was added in accordance with the electrolyte composition as shown in Table 1, wherein the content of each additive component was based on the total mass of the electrolyte.

The additives used are as follows:
Additive A:
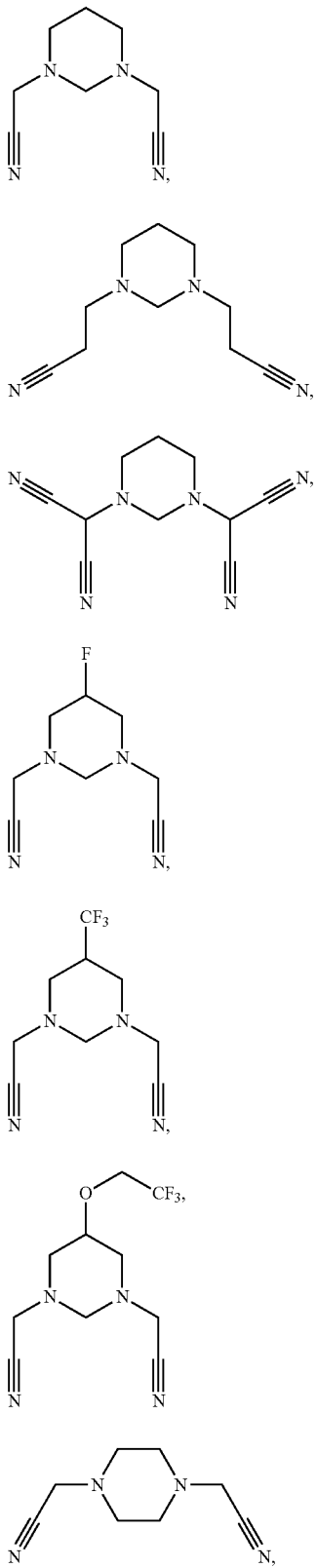
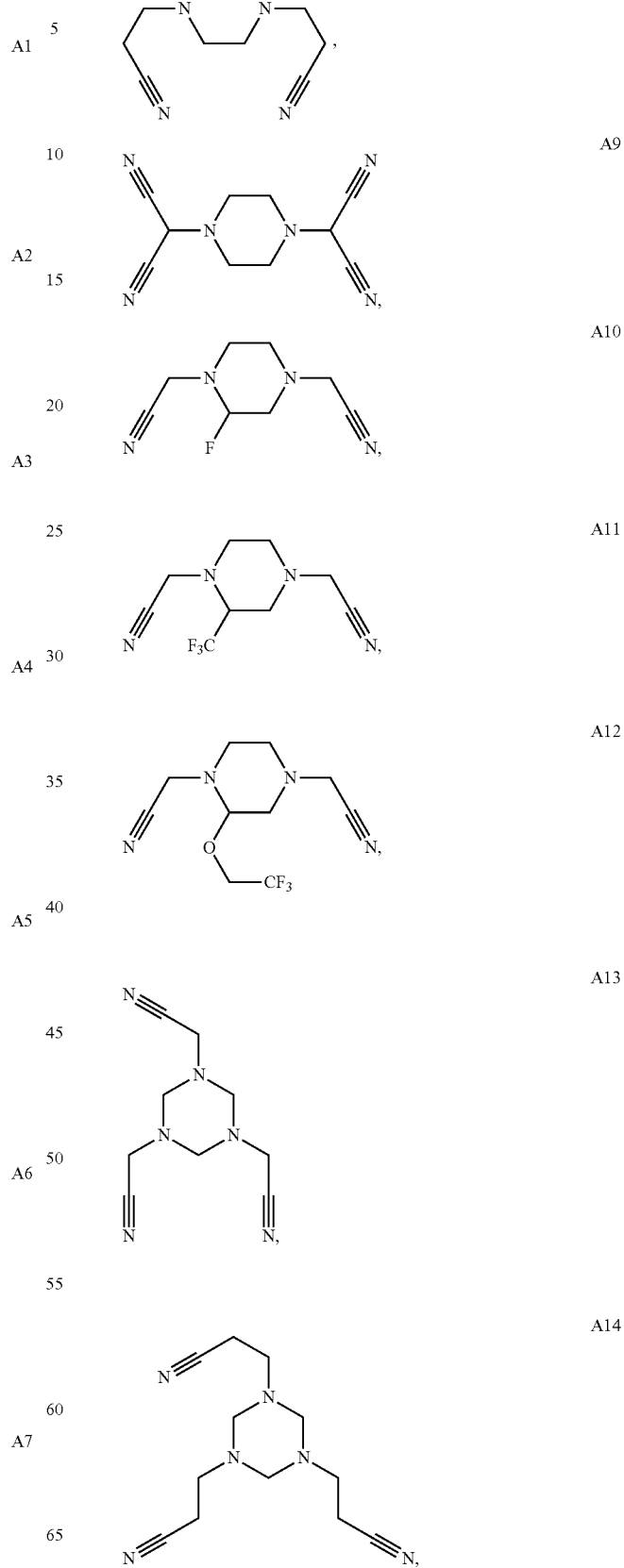

-continued

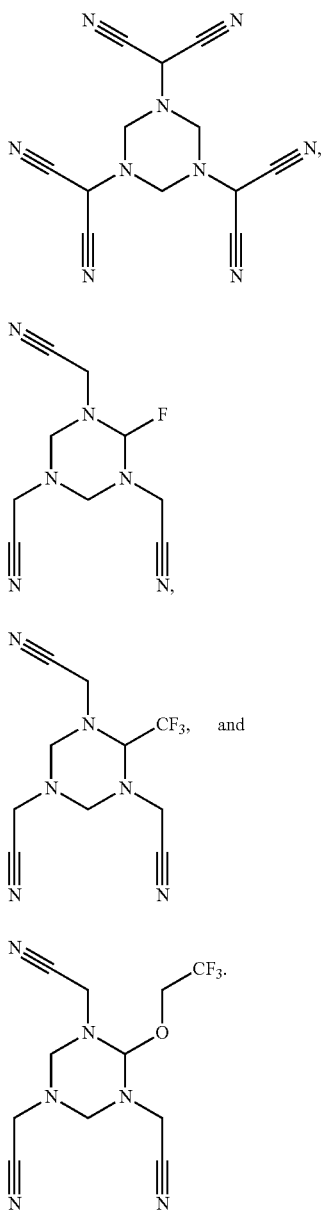

Additive B:

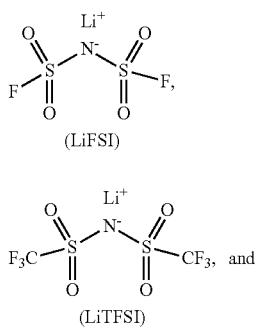

-continued

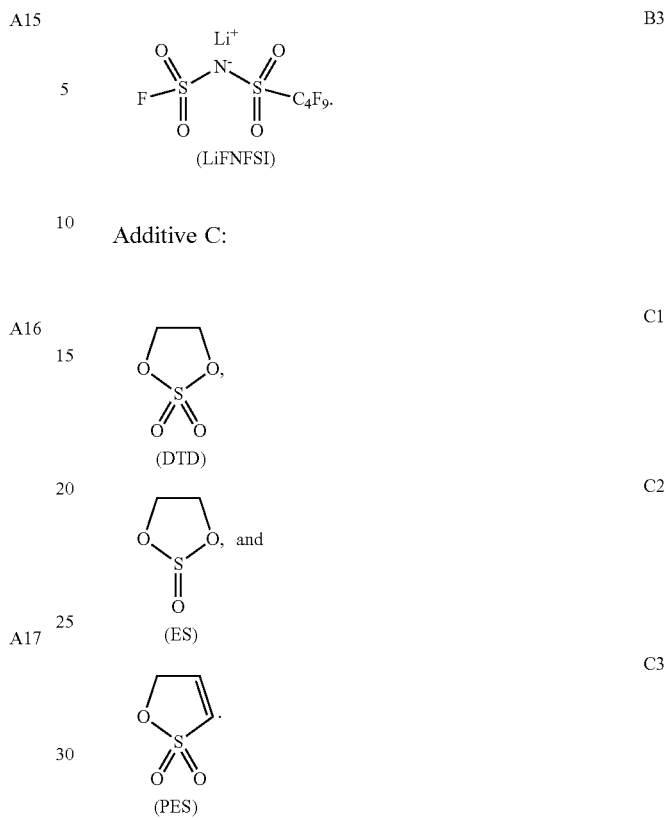

Additive C:

(2) Preparation of positive electrode plate: The positive active material $LiCoO_2$, the binder PVDF, the conductive agent acetylene black were mixed at a mass ratio of 98:1:1, then the N-methylpyrrolidone was added, and stirred under a vacuum stirrer until stable and uniform. The positive electrode slurry was obtained; then the positive electrode slurry was uniformly coated on the aluminum foil; the aluminum foil was air-dried at room temperature, and transferred to a blast oven to dry at 120° C. for 1 hour, and then subjected to cold pressing and slitting to obtain a positive electrode plate.

(3) Preparation of negative electrode plate: The negative active material graphite, the conductive agent acetylene black, the thickener carboxymethyl cellulose sodium solution, and the binder styrene-butadiene rubber emulsion are mixed at a mass ratio of 97:1:1:1, then deionized water was added, and stirred under a vacuum stirrer until stable and uniform. The negative electrode slurry was obtained; then the negative electrode slurry was uniformly coated on the copper foil; the copper foil was air-dried at room temperature, and transferred to a blast oven to dry at 120° C. for 1 hour, and then subjected to cold pressing and slitting to obtain a negative electrode plate.

(4) Preparation of lithium-ion secondary battery: The positive electrode plate, the negative electrode plate and the PP/PE/PP separator were wound to obtain a battery core, and after the battery core was placed in the package, the electrolyte was injected, and then the sealing was sequentially performed. A lithium-ion secondary battery was obtained by processes such as standing, hot-cold pressing, chemical formation, exhausting, and capacity test.

TABLE 1

Electrolyte parameters of Examples 1-25 and Comparative Examples 1-2

| | Solvent | Additive A Type | Additive A Content | Additive B Type | Additive B Content | Additive C Type | Additive C Content |
|---|---|---|---|---|---|---|---|
| Example 1 | EC:EMC:DEC = 1:1:1 | A1 | 0.001% | B1 | 10.0% | / | / |
| Example 2 | EC:EMC:DEC = 1:1:1 | A1 | 0.1% | B3 | 8.0% | / | / |
| Example 3 | EC:EMC:DEC = 1:1:1 | A1 | 1.0% | B2 | 6.0% | / | / |
| Example 4 | EC:EMC:DEC = 1:1:1 | A1 | 1.5% | B2 | 4.0% | / | / |
| Example 5 | EC:EMC:DEC = 1:1:1 | A1 | 2.0% | B1 | 4.0% | / | / |
| Example 6 | EC:EMC:DEC = 1:1:1 | A1 | 2.0% | B2 | 4.0% | / | / |
| Example 7 | EC:EMC:DEC = 1:1:1 | A1 | 2.0% | B3 | 4.0% | / | / |
| Example 8 | EC:EMC:DEC = 1:1:1 | A1 | 2.0% | B2 | 3.0% | / | / |
| Example 9 | EC:EMC:DEC = 1:1:1 | A1 | 4.0% | B3 | 2.0% | / | / |
| Example 10 | EC:EMC:DEC = 1:1:1 | A1 | 6.0% | B2 | 1.0% | / | / |
| Example 11 | EC:EMC:DEC = 1:1:1 | A1 | 8.0% | B1 | 0.1% | / | / |
| Example 12 | EC:EMC:DEC = 1:1:1 | A1 | 10.0% | B3 | 0.1% | / | / |
| Example 13 | EC:EMC:DEC = 1:1:1 | A1 | 2.0% | B1 | 4.0% | C2 | 0.1% |
| Example 14 | EC:EMC:DEC = 1:1:1 | A1 | 2.0% | B1 | 4.0% | C3 | 0.5% |
| Example 15 | EC:EMC:DEC = 1:1:1 | A1 | 2.0% | B1 | 4.0% | C1 | 2.0% |
| Example 16 | EC:EMC:DEC = 1:1:1 | A1 | 2.0% | B1 | 4.0% | C1 | 3.0% |
| Example 17 | EC:EMC:DEC = 1:1:1 | A1 | 2.0% | B1 | 4.0% | C2 | 4.0% |
| Example 18 | EC:EMC:DEC = 1:1:1 | A1 | 2.0% | B1 | 4.0% | C1 | 4.0% |
| Example 19 | EC:EMC:DEC = 1:1:1 | A1 | 2.0% | B1 | 4.0% | C3 | 4.0% |
| Example 20 | EC:EMC:DEC = 1:1:1 | A1 | 2.0% | B1 | 4.0% | C3 | 5.0% |
| Example 21 | EC:EMC:DEC = 1:1:1 | A1 | 2.0% | B1 | 4.0% | C1 | 6.0% |
| Example 22 | EC:EMC:DEC = 1:1:1 | A1 | 2.0% | B1 | 4.0% | C2 | 8.0% |
| Example 23 | EC:EMC:DEC = 1:1:1 | A1 | 2.0% | B1 | 4.0% | C1 | 10.0% |
| Example 24 | EC:EMC:DEC = 1:1:1 | A1 | 2.0% | B1 | 4.0% | C2 | 10.0% |
| Example 25 | EC:EMC:DEC = 1:1:1 | A1 | 2.0% | B1 | 4.0% | C3 | 10.0% |
| Comparative Example 1 | EC:EMC:DEC = 1:1:1 | / | / | / | / | / | / |
| Comparative Example 2 | EC:EMC:DEC = 1:1:1 | A1 | 2.0% | / | / | / | / |

The test process of the lithium-ion secondary battery is described below.

(1) Cyclic Performance Test of Lithium-Ion Secondary Battery Under Normal Temperature and High Voltage Conditions At 25° C., the lithium-ion secondary battery was first charged with a constant current of 1 C to a voltage of 4.35 V, further charged with a constant voltage of 4.35 V until the current was 0.05 C, and then discharged with a constant current of 1 C to a voltage of 3.0 V. Charging/discharging cycle was done in such way. The discharge capacity at this time was the discharge capacity of the first cycle. The lithium-ion secondary battery was subjected to 200 cycles of charge/discharge test in accordance with the above method, and the discharge capacity at the $200^{th}$ cycle was detected.

Capacity retention ratio (%) of lithium-ion secondary battery of the $200^{th}$ cycle=(discharge capacity of the $200^{th}$ cycle/discharge capacity of lithium-ion secondary battery at the first cycle)×100%.

(2) Cycle Performance Test of Lithium-Ion Secondary Battery Under High Temperature and High Voltage Conditions At 45° C., the lithium-ion secondary battery was first charged with a constant current of 1 C to a voltage of 4.35 V, further charged with a constant voltage of 4.35 V until the current was 0.05 C, and then discharged with a constant current of 1 C to a voltage of 3.0 V. Charging/discharging cycle was done in such way. The discharge capacity at this time was the discharge capacity of the first cycle. The lithium-ion secondary battery was subjected to 200 cycles of charge/discharge test in accordance with the above method, and the discharge capacity at the $200^{th}$ cycle was detected.

Capacity retention ratio (%) of lithium-ion secondary battery of the $200^{th}$ cycle=(discharge capacity of the $200^{th}$ cycle/discharge capacity of lithium-ion secondary battery at the first cycle)×100%.

(3) Storage Performance Test of Lithium-Ion Secondary Battery Under High Temperature Conditions At 25° C., the lithium-ion secondary battery was charged with a constant current of 0.5 C to a voltage of 4.35 V, and then charged with a constant voltage of 4.35 V until the current was 0.05 C. At this time, the thickness of the lithium-ion secondary battery was tested and recorded as $h_0$; then the lithium-ion was placed in an incubator at 85° C., and stored for 24 hours. Then the battery was taken out and the thickness of the lithium-ion secondary battery was measured and recorded as $h_1$.

The thickness expansion ratio (%) of the lithium-ion secondary battery after storage at 85° C. for 24 hours=[($h_1$−$h_0$)/$h_0$]×100%.

TABLE 2

Test results of Examples 1-25 and Comparative Examples 1-2

| | 25° C./4.35 V/ Capacity retention ratio (%) after 200 cycles | 45° C./4.35 V/ Capacity retention ratio (%) after 200 cycles | 85° C. 24 h Thickness expansion ratio |
|---|---|---|---|
| Example 1 | 76% | 59% | 45% |
| Example 2 | 84% | 72% | 15% |
| Example 3 | 92% | 86% | 9% |
| Example 4 | 95% | 90% | 7% |
| Example 5 | 95% | 93% | 5% |
| Example 6 | 96% | 93% | 6% |
| Example 7 | 95% | 92% | 5% |
| Example 8 | 95% | 91% | 6% |
| Example 9 | 93% | 88% | 4% |
| Example 10 | 88% | 83% | 3% |
| Example 11 | 84% | 76% | 1% |

TABLE 2-continued

Test results of Examples 1-25 and Comparative Examples 1-2

| | 25° C./4.35 V/ Capacity retention ratio (%) after 200 cycles | 45° C./4.35 V/ Capacity retention ratio (%) after 200 cycles | 85° C.24 h Thickness expansion ratio |
|---|---|---|---|
| Example 12 | 75% | 62% | 1% |
| Example 13 | 96% | 93% | 5% |
| Example 14 | 96% | 93% | 4% |
| Example 15 | 98% | 95% | 3% |
| Example 16 | 99% | 96% | 3% |
| Example 17 | 97% | 95% | 2% |
| Example 18 | 98% | 96% | 2% |
| Example 19 | 97% | 93% | 2% |
| Example 20 | 95% | 89% | 1% |
| Example 21 | 93% | 85% | 2% |
| Example 22 | 89% | 81% | 3% |
| Example 23 | 81% | 75% | 1% |
| Example 24 | 82% | 72% | 2% |
| Example 25 | 76% | 69% | 1% |
| Comparative Example 1 | 83% | 75% | 67% |
| Comparative Example 2 | 94% | 91% | 7% |

The addition of the additive A to the electrolyte can effectively improve the gas generation problem of the lithium-ion secondary battery, optimize the storage performance, and further increase the cycle performance of the lithium-ion secondary battery at 25° C. and at 45° C. The mechanism of such action is mainly to reduce the surface activity of positive active material, suppress the side reaction between the positive active material and the electrolyte, thereby reducing the gas production, reducing the capacity loss, and thereby exhibiting excellent cycle performance and storage performance.

On the basis of the additive A, the addition of the appropriate ratio of the additive B (i.e., the sulfonimide lithium salt) further improves the cycle performance and storage performance of the lithium-ion secondary battery under high temperature and high voltage conditions, and further reduces the gas production. The main mechanism of such action is that, the additive A can stabilize the surface of the positive electrode and reduce the occurrence of side reactions on the surface of the positive electrode; while on the one hand the additive B has the characteristics of high decomposition temperature and no HF during decomposition, that is to say, the thermal stability of the additive B is significantly stronger than $LiPF_6$. Thus it can significantly improve the cycle performance and storage performance of the battery. On the other hand, it can also participate in the formation of the SEI film on the negative electrode, so that the formed SEI film can isolate the negative electrode from directly contacting with the electrolyte, thereby effectively reducing the occurrence of side reactions, and finally further improving the cycle performance and storage performance of lithium-ion secondary batteries.

Examples 1-12 show the effects of the interaction of different ratios of additive A to additive B on the performance of a lithium-ion secondary battery. It can be seen from Example 1 that when the additive A is added in a small amount and the additive B is added in a large amount, the cycle performance of the lithium-ion secondary battery is deteriorated, and the gas generation problem is improved to some extent, but the improvement effect is not large. The reason is that: when the additive A is added in a small amount, the protection effect of the additive A on the positive active material is not obvious, and if the additive B is added in a large amount, a strong aluminum foil corrosion phenomenon occurs at a high voltage, thereby causing the deterioration of cycle performance. With the increase of the addition amount of additive A and the decrease of the addition amount of additive B, the synergistic effect of the additive A and the additive B on the lithium-ion secondary battery is gradually manifested. When the additive A is added in an amount of 2% and the additive B is added in an amount of 4%, the cycle performance and storage performance of the lithium-ion secondary battery are also greatly improved compared with the comparative example 2. Example 5, Example 6, and Example 7 show the optimal ratios of three sulfonimide lithium salts LiFSI, LiTFSI and LiFNFSI to the additive A, respectively, which all make the cycle performance and storage performance of the lithium-ion secondary battery have great improvement.

Experimental Example 13-25 explored the addition amount of the additive C (sulfate, sulfite, sulfonate) and the effect thereof on the lithium-ion secondary battery under the optimal conditions of the addition amount of the additive A and the additive B, wherein we choose additive B1 (LiFSI) which has better optimization effect on the cycle performance and storage performance, as a base additive. In the examples 13-25, the additive C is added in an amount ranging from 0.1% to 10%. The additive C (i.e. any one of a sulfate, a sulfite, and a sulfonate) is a good negative electrode film-forming additive, which preferentially forms a film on the negative electrode than the other substances in the electrolyte (for example, an organic solvent) to prevent the destruction of the graphite structure caused by the organic solvent and the solvated lithium ion, but if the addition amount of the additive C is too high, the battery impedance is increased, and the cycle performance and storage performance will be deteriorated. It can be seen from Examples 13-25 that when the additive C is added in a small amount (less than 1%), the performance of the lithium-ion secondary battery is not significantly improved as compared with Example 5, due to that the amount of the additive C participating in the film formation is small, it is difficult to play a significant role; when the additive C is added in a large amount (greater than 6%), the thickness of the formed SEI film is likely to be large. Thus on the one hand the migration speed of lithium ions will be lowered, the battery impedance will be increased and even lithium precipitation will be caused. On the other hand, more film formation reactions consume a large amount of lithium ions, resulting in a significant increase in irreversible capacity and a significant decrease in cycle performance. When the addition amount of the additive C is 4%, the cycle performance and storage performance of the lithium-ion secondary battery are optimized. Example 17, Example 18, and Example 19 show the battery performance with the optimal addition amounts of additive C2 (cyclic sulfite, ES), additive C1 (cyclic sulfate, DTD), and additive C3 (sultone, PES), respectively. It can be seen that the additive C1 (cyclic sulfite, DTD) is superior to the other two types of additives in improving the cycle capacity retention ratio and gas generation problem.

Other Examples

A lithium-ion secondary battery was further prepared by the method of the above Examples 1-25, and the composition of the electrolyte was as shown in Table 3.

TABLE 3

Electrolyte parameters of Examples 26-42

| | Organic solvent | Additive A Type | Additive A Content | Additive B Type | Additive B Content | Additive C Type | Additive C Content |
|---|---|---|---|---|---|---|---|
| Example 26 | EC:EMC:DEC = 1:1:1 | A2 | 2.0% | B1 | 4.0% | / | / |
| Example 27 | EC:EMC:DEC = 1:1:1 | A3 | 2.0% | B2 | 4.0% | / | / |
| Example 28 | EC:EMC:DEC = 1:1:1 | A4 | 2.0% | B1 | 4.0% | / | / |
| Example 29 | EC:EMC:DEC = 1:1:1 | A5 | 2.0% | B2 | 4.0% | / | / |
| Example 30 | EC:EMC:DEC = 1:1:1 | A6 | 2.0% | B1 | 4.0% | / | / |
| Example 31 | EC:EMC:DEC = 1:1:1 | A7 | 2.0% | B2 | 4.0% | / | / |
| Example 32 | EC:EMC:DEC = 1:1:1 | A8 | 2.0% | B1 | 4.0% | C1 | 3.0% |
| Example 33 | EC:EMC:DEC = 1:1:1 | A9 | 2.0% | B2 | 4.0% | C2 | 3.0% |
| Example 34 | EC:EMC:DEC = 1:1:1 | A10 | 2.0% | B1 | 4.0% | C3 | 3.0% |
| Example 35 | EC:EMC:DEC = 1:1:1 | A11 | 2.0% | B2 | 4.0% | C3 | 3.0% |
| Example 36 | EC:EMC:DEC = 1:1:1 | A12 | 2.0% | B1 | 4.0% | C1 | 3.0% |
| Example 37 | EC:EMC:DEC = 1:1:1 | A13 | 2.0% | B2 | 4.0% | C2 | 3.0% |
| Example 38 | EC:EMC:DEC = 1:1:1 | A14 | 2.0% | B1 | 4.0% | C3 | 3.0% |
| Example 39 | EC:EMC:DEC = 1:1:1 | A15 | 2.0% | B1 | 4.0% | C2 | 3.0% |
| Example 40 | EC:EMC:DEC = 1:1:1 | A16 | 2.0% | B1 | 4.0% | C1 | 3.0% |
| Example 41 | EC:EMC:DEC = 1:1:1 | A17 | 2.0% | B1 | 4.0% | C1 | 3.0% |
| Example 42 | EC:EMC:DEC = 1:1:1 | A18 | 2.0% | B1 | 4.0% | C1 | 3.0% |

TABLE 4

Test results of Examples 26-42

| | 25° C./4.35 V/Capacity retention ratio (%) after 200 cycles | 45° C./4.35 V/Capacity retention ratio (%) after 200 cycles | 85° C. 24 h Thickness expansion ratio |
|---|---|---|---|
| Example 26 | 95% | 92% | 5% |
| Example 27 | 94% | 91% | 6% |
| Example 28 | 94% | 92% | 7% |
| Example 29 | 95% | 92% | 6% |
| Example 30 | 96% | 92% | 6% |
| Example 31 | 93% | 91% | 7% |
| Example 32 | 98% | 95% | 2% |
| Example 33 | 96% | 93% | 4% |
| Example 34 | 98% | 95% | 3% |
| Example 35 | 97% | 95% | 3% |
| Example 36 | 97% | 94% | 2% |
| Example 37 | 97% | 94% | 3% |
| Example 38 | 98% | 96% | 3% |
| Example 39 | 97% | 94% | 4% |
| Example 40 | 98% | 94% | 2% |
| Example 41 | 99% | 95% | 2% |
| Example 42 | 97% | 94% | 1% |

The cycle performance and storage performance of the lithium-ion secondary batteries of Examples 26-42 at high temperature and high voltage are similar to those of Examples 1-25, and are not described herein again.

It will be apparent to those skilled in the art that the present application may be modified and varied in accordance with the above teachings. Accordingly, the present application is not limited to the specific embodiments disclosed and described above, and modifications and variations of the present application are intended to be included within the scope of the claims of the present application. In addition, although some specific terminology is used in this specification, these terms are for convenience of illustration only and are not intended to limit the present application in any way.

The invention claimed is:

1. An electrolyte, wherein the electrolyte comprises an additive A and an additive B; and wherein the additive A is one or more selected from the group consisting of the following compounds:

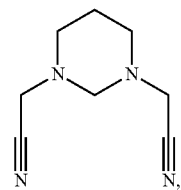

Formula I-1-1

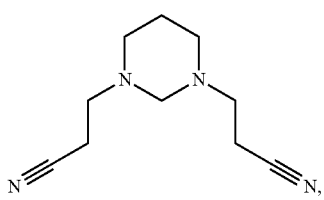

Formula I-1-2

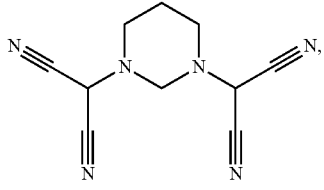

Formula I-1-3

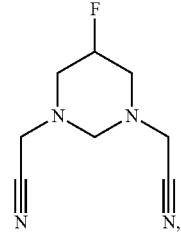

Formula I-1-4

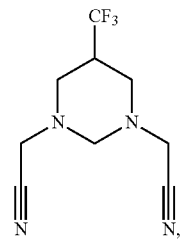

Formula I-1-5

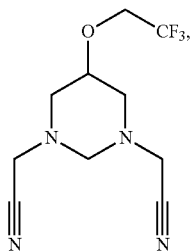
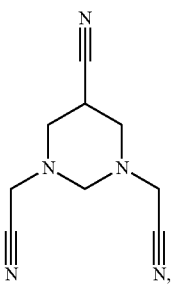
Formula I-1-6
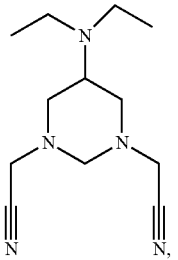
Formula I-1-7
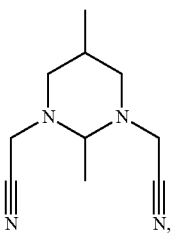
Formula I-1-8
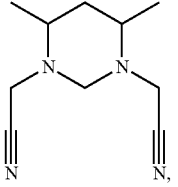
Formula I-1-9
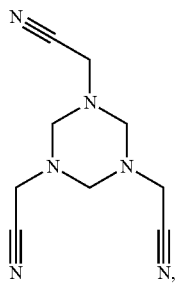
Formula I-1-10
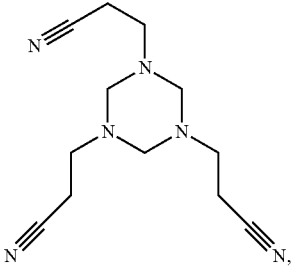
Formula I-1-11
Formula I-1-12
Formula I-1-13
Formula I-1-14
Formula I-3-1
Formula I-3-2

-continued

Formula I-3-3
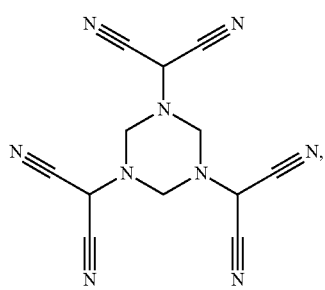

Formula I-3-4
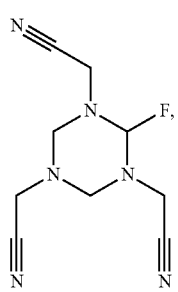

Formula I-3-5
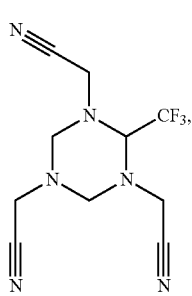

Formula I-3-6
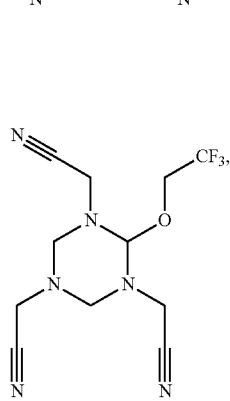

Formula I-3-7
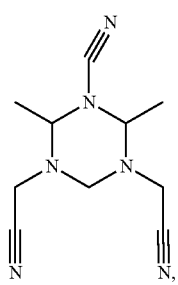

Formula I-3-8
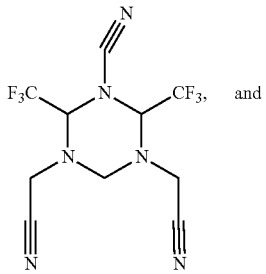
and

Formula I-3-9
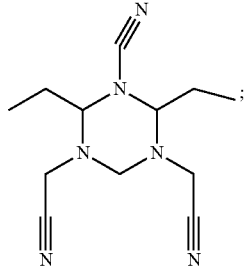
;

and
wherein the additive B is selected from a sulfonimide lithium salt represented by Formula II; in Formula II, $R_F$ is one of $C_{p1}F_{2p1+1}$ and $F(CF_2CF_2O)_{q1}CF_2CF_2$, $R_f$ is one of $C_{p2}F_{2p2+1}$ and $F(CF_2CF_2O)_{q2}CF_2CF_2$, p1 and p2 are each independently selected from an integer of 0 to 8; and q1 and q2 are each independently selected from an integer of 1 to 6

Formula II
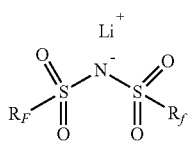

wherein the electrolyte comprises the additive A in an amount of 0.001% to 10% by mass of the electrolyte;
wherein the electrolyte comprises the additive B in an amount of 0.1% to 10% by mass of the electrolyte.

2. The electrolyte according to claim 1, wherein the electrolyte comprises the additive A in an amount of 0.01% to 6% by mass of the electrolyte.

3. The electrolyte according to claim 1, wherein the additive B is one or more selected from the group consisting of the following compounds:

Formula II-1
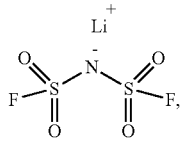

Formula II-2
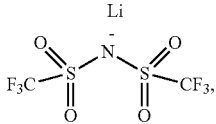

-continued

Formula II-3

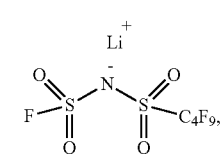

Formula II-4

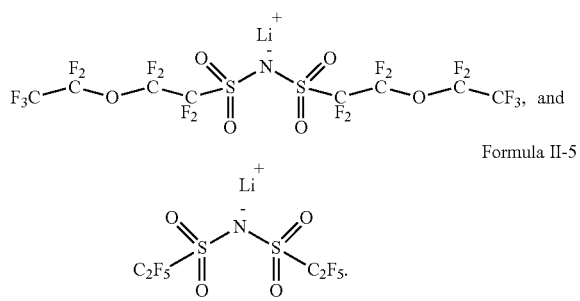

Formula II-5

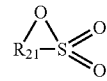

4. The electrolyte according to claim 1, wherein the electrolyte comprises the additive B in an amount of 0.5% to 6% by mass of the electrolyte.

5. The electrolyte according to claim 1, wherein the electrolyte further comprises an additive C which is one or more selected from the group consisting of a sulfate, a sulfite, and a sulfonate compound, wherein sulfonate compound is one or more selected from the group consisting of a sultone compound and a disulfonate compound;

wherein the sulfate compound is a cyclic sulfate compound, and the cyclic sulfate compound may be selected from one or more of the compounds represented by Formula III-1; in Formula III-1, $R_{31}$ is one or more selected from the group consisting of a substituted or unsubstituted $C_1$-$C_6$ alkylene group, and a substituted or unsubstituted $C_2$-$C_6$ alkenylene group, wherein the substituent is one or more selected from the group consisting of a halogen atom, a $C_1$-$C_3$ alkyl group, and a $C_2$-$C_4$ alkenyl group; and Formula III-1

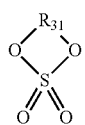

wherein the sulfite compound is a cyclic sulfite compound selected from one or more of the compounds represented by Formula III-2; in Formula III-2, $R_{32}$ is one or more selected from the group consisting of a substituted or unsubstituted $C_1$-$C_6$ alkylene group, and a substituted or unsubstituted $C_2$-$C_6$ alkenylene group, wherein the substituent is one or more selected from the group consisting of a halogen atom, a $C_1$-$C_3$ alkyl group, and a $C_2$-$C_4$ alkenyl group; and Formula III-2

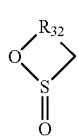

wherein the sultone compound is selected from one or more of the compounds represented by Formula III-3, and in Formula III-3, $R_{21}$ is one or more selected from the group consisting of a substituted or unsubstituted $C_1$-$C_6$ alkylene group, and a substituted or unsubstituted $C_2$-$C_6$ alkenylene group, wherein the substituent is one or more selected from the group consisting of a halogen atom, a $C_1$-$C_3$ alkyl group, and a $C_2$-$C_4$ alkenyl group; and Formula III-3

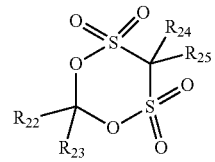

wherein the disulfonate compound is a compound selected from one or more of the compounds represented by Formula III-4; in Formula III-4, $R_{22}$, $R_{23}$, $R_{24}$ and $R_{25}$ are each independently one or more selected from the group consisting of a hydrogen atom, a halogen atom, a substituted or unsubstituted $C_1$-$C_{10}$ alkyl group, and a substituted or unsubstituted $C_2$-$C_{10}$ alkenyl group, wherein the substituent is one or more selected from the group consisting of a halogen atom, a $C_1$-$C_3$ alkyl group, and a $C_2$-$C_4$ alkenyl group;

Formula III-4 wherein the electrolyte comprises the additive C in an amount of 0.1% to 10% by mass of the electrolyte.

6. The electrolyte according to claim 5, wherein the electrolyte comprises the additive C in an amount of 0.5% to 6% by mass of the electrolyte.

7. The electrolyte according to claim 5, wherein the electrolyte comprises the additive C in an amount of 1% to 4% by mass of the electrolyte.

8. An electrochemical device comprising a positive electrode plate, a negative electrode plate, a separator disposed between the positive electrode plate and the negative electrode plate, and an electrolyte, wherein the electrolyte is the electrolyte according to claim 1.

9. The electrochemical device according to claim 8, wherein the electrochemical device is a lithium-ion secondary battery, a lithium primary battery, or a lithium-ion capacitor.

10. The electrolyte according to claim 1, wherein the electrolyte comprises the additive A in an amount of 0.1% to 3.5% by mass of the electrolyte.

11. The electrolyte according to claim 1, wherein the electrolyte comprises the additive B in an amount of 1% to 4% by mass of the electrolyte.

* * * * *